(12) United States Patent
Song

(10) Patent No.: US 10,123,774 B2
(45) Date of Patent: Nov. 13, 2018

(54) ULTRASONIC PROBE

(71) Applicant: SAMSUNG MEDISON CO., LTD., Gangwon-do (KR)

(72) Inventor: In Seong Song, Daegu (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 972 days.

(21) Appl. No.: 14/591,895

(22) Filed: Jan. 7, 2015

(65) Prior Publication Data

US 2015/0190116 A1  Jul. 9, 2015

(30) Foreign Application Priority Data

Jan. 7, 2014 (KR) .................. 10-2014-0002007

(51) Int. Cl.
- *A61B 8/00* (2006.01)
- *B06B 1/06* (2006.01)
- *G10K 11/32* (2006.01)

(52) U.S. Cl.
CPC .......... *A61B 8/4488* (2013.01); *A61B 8/4494* (2013.01); *B06B 1/0622* (2013.01); *G10K 11/32* (2013.01); *A61B 8/469* (2013.01)

(58) Field of Classification Search
CPC ..... A61B 8/4488; A61B 8/4494; A61B 8/469; B06B 1/0622; G10K 11/32
See application file for complete search history.

(56) References Cited

U.S. PATENT DOCUMENTS

| 5,570,691 | A | 11/1996 | Wright et al. |
| 6,106,467 | A | 8/2000 | Shimizu |
| 2005/0124889 | A1 | 6/2005 | Flesch |
| 2013/0060140 | A1 | 3/2013 | Sinelnikov |
| 2013/0190625 | A1* | 7/2013 | Shibamoto ............. A61B 8/546 600/447 |

(Continued)

FOREIGN PATENT DOCUMENTS

| CN | 1741770 A | 3/2006 |
| CN | 103181785 A | 7/2013 |
| EP | 1079369 A2 | 2/2001 |

(Continued)

OTHER PUBLICATIONS

Extended European Search Report issued in Application No. 14187033.7 dated Jun. 5, 2015.

(Continued)

*Primary Examiner* — Joel Lamprecht
(74) *Attorney, Agent, or Firm* — McDermott Will & Emery LLP

(57) ABSTRACT

Disclosed herein is an ultrasonic probe. The ultrasonic probe includes a matching layer having flexibility, a piezoelectric layer disposed on the bottom surface of the matching layer and having flexibility, a first backing layer disposed on the bottom surface of the piezoelectric layer and having flexibility, a second backing layer disposed on the bottom surface of the first backing layer and including a plurality of backing material layers stacked perpendicularly to the first backing layer, and second backing layer adjusting units respectively disposed between every two of the plurality of the stacked backing material layers of the second backing layer and changing the shape of the backing material layers.

15 Claims, 26 Drawing Sheets

(56) References Cited

U.S. PATENT DOCUMENTS

2015/0216504 A1\* 8/2015 Kiyose .................. B06B 1/0629
600/472

FOREIGN PATENT DOCUMENTS

| JP | 07-275250 A | 10/1995 |
|---|---|---|
| JP | 08-289386 A | 11/1996 |
| WO | 01/45550 A2 | 6/2001 |

OTHER PUBLICATIONS

Chinese Office Action dated Aug. 20, 2018 issued in Chinese Patent Application No. 201510004736.0 (with English translation).

\* cited by examiner

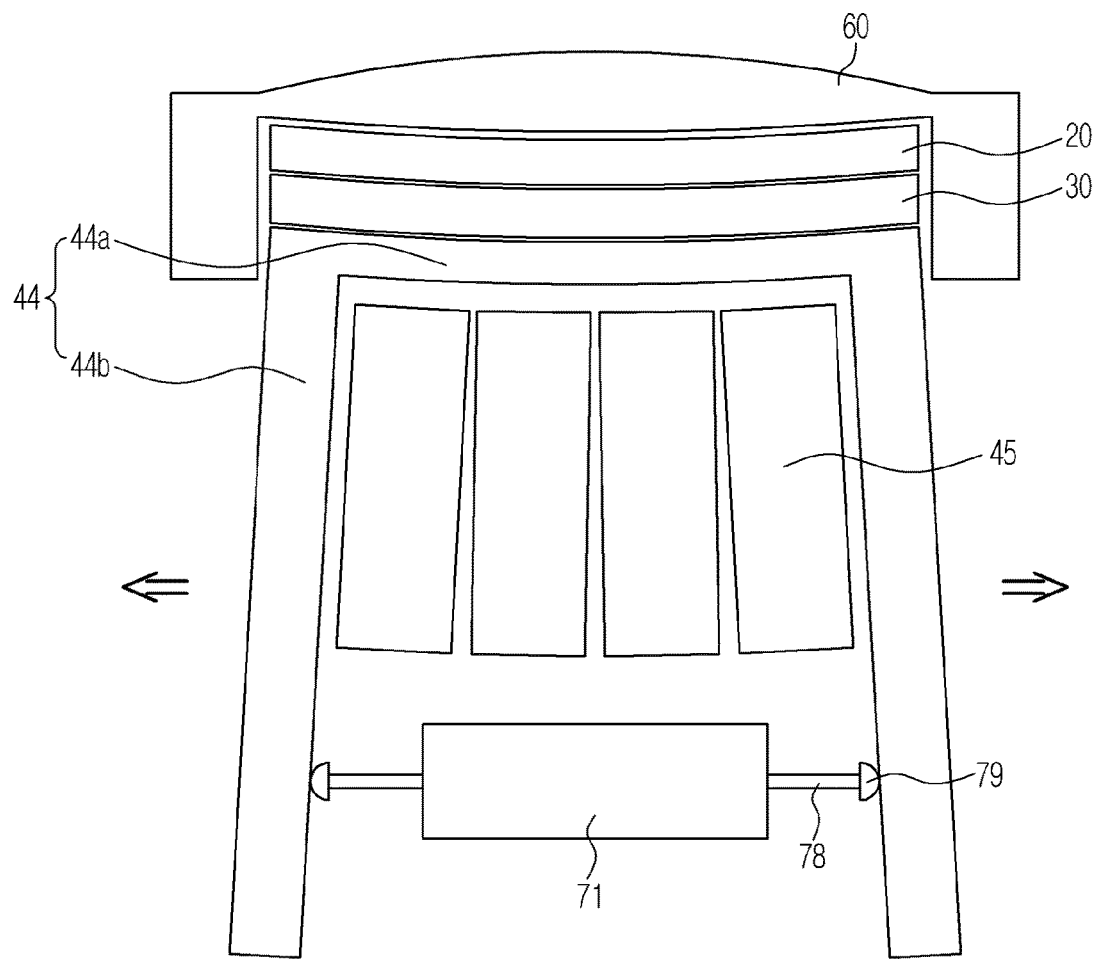

ULTRASONIC PROBE

CROSS-REFERENCE TO RELATED
APPLICATION(S)

This application claims the benefit of Korean Patent Application No. 2014-0002007, filed on Jan. 7, 2014 in the Korean Intellectual Property Office, the disclosure of which is incorporated herein by reference.

BACKGROUND

1. Field

Embodiments of the present invention relate to an ultrasonic probe having improved resolution by changing a focal zone by modifying a shape of a backing layer.

2. Description of the Related Art

An ultrasonic diagnostic apparatus emits ultrasonic signals toward a target region of an object from the surface of the object and generates an image of the target region such as a soft tissue tomogram or a blood stream image using reflected ultrasonic signals, i.e., ultrasonic echo signals. Since the ultrasonic diagnostic apparatus is small and inexpensive, displays an image in real time, and provides high safety owing to no X-ray exposure, or the like, as compared to other image diagnostic apparatuses such as an X-ray diagnostic apparatus, a computed tomography (CT) scanner, a magnetic resonance imaging (MRI) apparatus, and a nuclear medicine diagnostic apparatus, the ultrasonic diagnostic apparatus is widely used for heart diagnosis, celiac diagnosis, urinary diagnosis, and obstetric diagnosis.

The ultrasonic diagnostic apparatus includes an ultrasonic probe to transmit ultrasonic signals to an object and receive ultrasonic echo signals reflected by the object in order to acquire an ultrasonic image of the object.

The ultrasonic probe includes an acoustic module. In this regard, a transducer may include a piezoelectric layer to perform interconversion between an electric signal and an acoustic signal while a piezoelectric material vibrates, a matching layer to reduce difference in acoustic impedance between the piezoelectric layer and the object thereby efficiently transfer ultrasonic waves generated by the piezoelectric layer to the object, a lens layer to focus ultrasonic waves proceeding forward from the piezoelectric layer on a predetermined point, a backing layer to block transmission of the ultrasonic waves proceeding backward from the piezoelectric layer thereby preventing image distortion.

SUMMARY

Therefore, it is an aspect of the present invention to provide an ultrasonic probe having a focal zone adjusted by changing curvatures of a matching layer and a piezoelectric layer disposed on a backing layer in accordance with a changed curvature of the backing layer.

Additional aspects of the invention will be set forth in part in the description which follows and, in part, will be obvious from the description, or may be learned by practice of the invention.

In accordance with one aspect of the present invention, an ultrasonic probe includes a matching layer having flexibility, a piezoelectric layer disposed on the bottom surface of the matching layer and having flexibility, a first backing layer disposed on the bottom surface of the piezoelectric layer and having flexibility, a second backing layer disposed on the bottom surface of the first backing layer and including a plurality of backing material layers stacked perpendicularly to the first backing layer, and second backing layer adjusting units respectively disposed between every two of the plurality of the stacked backing material layers of the second backing layer and changing an interval between the backing material layers.

In accordance with another aspect of the present invention, an ultrasonic probe includes a matching layer having flexibility, a piezoelectric layer disposed on the bottom surface of the matching layer and having flexibility, a first backing layer disposed on the bottom surface of the piezoelectric layer, including a ceiling disposed parallel to the piezoelectric layer and barrier walls disposed perpendicularly to the piezoelectric layer, and having flexibility, a second backing layer disposed on the bottom surface of the first backing layer and including a plurality of backing material layers stacked perpendicularly to the first backing layer, and a first backing layer adjusting unit disposed in a space defined by a bottom surface of the second backing layer and the barrier walls of the first backing layer, and changing the shape of the first backing layer.

Among a plurality of backing material layers of the second backing layer, a central backing material layer may be fixed to the first backing layer not to move horizontally or may move vertically to adjust a width of the backing layer.

The piezoelectric layer may be formed of a ceramic complex, and the piezoelectric layer may include a plurality of piezoelectric layers arranged in a matrix array, a linear array, a convex array, a phased array, or a concave array.

The ultrasonic probe may include a controller to control operations of backing layer adjusting units and the piezoelectric layer, and the controller may adjust focal zones of ultrasonic waves.

BRIEF DESCRIPTION OF THE DRAWINGS

These and/or other aspects of the invention will become apparent and more readily appreciated from the following description of the embodiments, taken in conjunction with the accompanying drawings of which:

FIG. 10B is a conceptual diagram illustrating a method of increasing a curvature of a first backing layer of an ultrasonic probe in which the first backing layer includes barrier walls, without vertical movement of a first backing layer adjusting unit according to an embodiment of the present invention;

DETAILED DESCRIPTION

Figure 1:
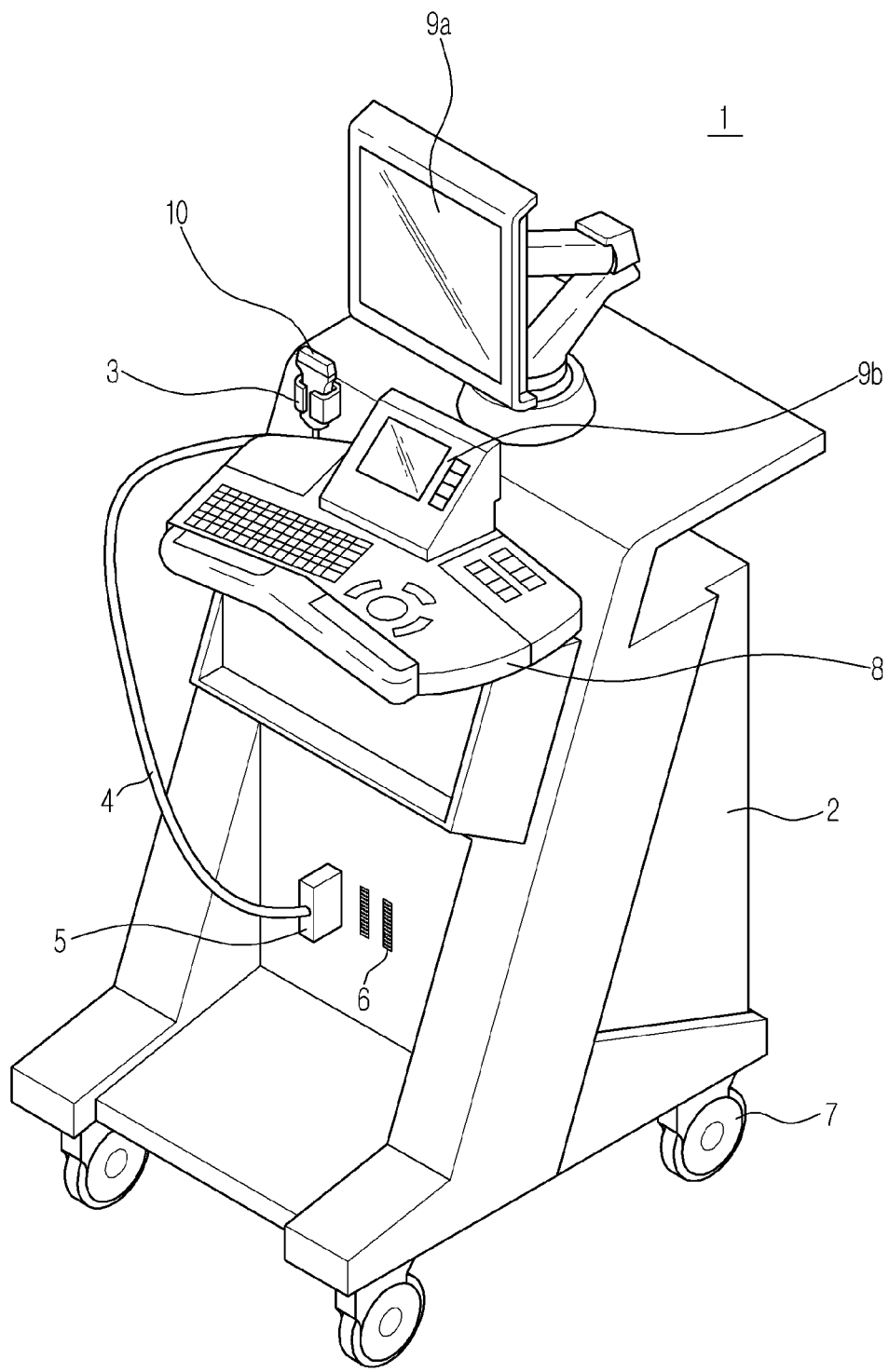
FIG. 1 is a perspective view illustrating an ultrasonic diagnostic apparatus including an ultrasonic probe according to an embodiment of the present invention.

Reference will now be made in detail to the embodiments of the present invention, examples of which are illustrated in the accompanying drawings, wherein like reference numerals refer to like elements throughout.

Further, the following terms, which are defined in consideration of functions of the present invention, may be altered depending on the user's intentions or judicial precedents. Therefore, the meaning of each term should be interpreted based on the content of the entire disclosure of the specification. If there is no specific definition, the terms should be interpreted as generally interpreted by one of ordinary skill in the art.

Unless defined otherwise, all constituent elements according to aspects and embodiments of the present invention may be combined with each other, if it is obvious to one of ordinary skill in the art that combinations thereof are not technically contradictory, although a single integrated configuration thereof is illustrated in the drawings.

Hereinafter an ultrasonic probe according to an embodiment of the present invention will be described with reference to the accompanying drawings.

Referring to FIG. 1, an ultrasonic diagnostic apparatus including an ultrasonic probe will be described.

FIG. 1 illustrates an appearance of an ultrasonic diagnostic apparatus 1 including an ultrasonic probe.

The ultrasonic diagnostic apparatus 1 includes a main body 2, an ultrasonic probe 10, input unit 8, a sub display unit 9b, and a main display unit 9a.

The main body 2 may accommodate a transmit signal generator of the ultrasonic diagnostic apparatus 1. When an examiner inputs an instruction to initiate an ultrasonic diagnosis, the transmit signal generator may generate a transmit signal and transmit the generated transmit signal to the ultrasonic probe 10.

More than one female connector 6 may be provided at one side of the main body 2. A male connector 5 connected to a cable 4 may be physically coupled to the female connector 6. The transmit signal generated by the transmit signal generator may be transmitted to the ultrasonic probe 10 via the male connector 5 coupled to the female connector 6 of the main body 2 and the cable 4.

Meanwhile, a plurality of casters 7 may be provided at the bottom of the main body 2 to provide mobility of the ultrasonic diagnostic apparatus 1. The plurality of casters 7 may fix the ultrasonic diagnostic apparatus 1 at a particular place, or may allow the ultrasonic diagnostic apparatus 1 to be moved in a particular direction.

The ultrasonic probe 10 that contacts the surface of the body of an object may transmit and receive ultrasonic waves. Particularly, the ultrasonic probe 10 converts a signal received from the main body 2 into an ultrasonic signal, emits the converted ultrasonic signal into the body of the object, receives an ultrasonic echo signal reflected by a particular region inside the object, and transmits the received signal to the main body 2.

To this end, a plurality of acoustic modules that generates ultrasonic waves in accordance with electric signals are provided at one end of the ultrasonic probe 10.

The acoustic modules may generate ultrasonic waves in accordance with applied alternating current (AC) power. Particularly, the acoustic modules may be receive AC power from an external power supply or an internal capacitor. A piezoelectric layer 30 of the acoustic module may vibrate in accordance with the received AC powder, thereby generating ultrasonic waves.

The plurality of acoustic modules may be arranged in a matrix array, a linear array, or a convex array. The plurality of acoustic modules may also be arranged in a phased array or a concave array. In addition, a cover to cover the acoustic modules may be provided at upper portions of the acoustic modules.

One end of the cable 4 may be connected to the other end of the ultrasonic probe 10, and the other end of the cable 4 may be connected to the male connector 5. The male connector 5 may physically be coupled to the female connector 6.

The input unit 8 may receive an instruction related to operation of the ultrasonic diagnostic apparatus 1. For example, the ultrasonic diagnostic apparatus 1 may receive an instruction to select a mode such as an amplitude mode (A-mode), a brightness mode (B-mode), and a motion mode (M-mode), or an instruction to initiate an ultrasonic diagnosis via the input unit 8. The instruction input through the input unit 8 may be transmitted to the main body 2 via a wireless or wired communication network.

The input unit 8 may include at least one of a touchpad, a keyboard, a foot switch, a foot pedal. The touchpad or keyboard may be a hardware element located at an upper portion of the main body 2. The keyboard may include at least one of a switch, a key, a wheel, a joystick, a trackball, and a knop. As another example, the keyboard may also be a software element such as a graphic user interface. In this case, the keyboard may be displayed via the sub display unit 9b or the main display unit 9a. The foot switch or foot pedal may be provided at a lower portion of the main body 2, and a manipulator may control operation of the ultrasonic diagnostic apparatus 1 using the foot pedal.

A probe holder 3 in which the ultrasonic probe 10 is placed may be provided near the input unit 8. The ultrasonic probe 10 may be held by the probe holder 3 for storage when the ultrasonic diagnostic apparatus 1 is not in use. Although one probe holder 3 is provided near the input unit 8 in FIG. 1, embodiments of the present invention are not limited thereto. The location and number of the probe holder 3 may vary according to a design of the ultrasonic diagnostic apparatus 1 and designs or locations of components thereof.

The sub display unit 9b may be provided at the main body 2. FIG. 1 illustrates that the sub display unit 9b is located above the input unit 8. The sub display unit 9b may be implemented using a cathode ray tube (CRT), a liquid crystal display (LCD), and the like. The sub display unit 9b may display menus or guidelines required for ultrasonic diagnosis.

The main display unit 9a may be provided at the main body 2. FIG. 1 illustrates that the main display unit 9a is located above the sub display unit 9b. The main display unit 9a may be implemented using a CRT or a LCD. The main display 9a may display an ultrasound image acquired during the ultrasonic diagnosis. The ultrasound image displayed through the main display unit 9a may include at least one of a two-dimensional (2D) black and white ultrasound image, a 2D color ultrasound image, a three-dimensional (3D) black and white ultrasound image, and a 3D color ultrasound image.

Although FIG. 1 illustrates that the ultrasonic diagnostic apparatus 1 includes both the sub display unit 9b and the main display unit 9a. If required, the sub display unit 9b may not be used. In this case, applications or menus displayed through the sub display unit 9b may be displayed through the main display unit 9a.

In addition, at least one of the sub display unit 9b and the main display unit 9a may be implemented in a state of being separated from the main body 2.

Hereinafter an acoustic module of the ultrasonic probe according to an embodiment of the present invention will be described with reference to FIG. 2.

Figure 2:
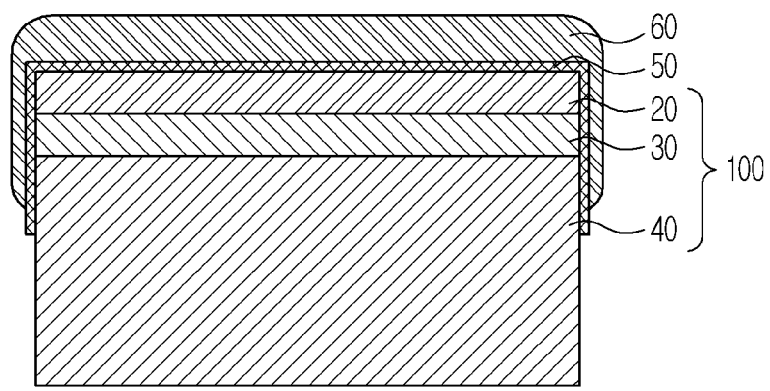
FIG. 2 is a cross-sectional view illustrating an acoustic module mounted in an ultrasonic probe according to an embodiment of the present invention.

FIG. 2 illustrates a cross-sectional view of an acoustic module provided in the ultrasonic probe.

As illustrated in FIG. 2, the ultrasonic probe may include an acoustic module 100, which includes a piezoelectric layer 30, a backing layer 40 disposed on the bottom surface of the piezoelectric layer 30, and a matching layer 20 disposed on the top surface of the piezoelectric layer 30, a protective layer 50 to cover the top surface and portions of the side surfaces of the acoustic module 100, and a lens layer 60 to cover the top surface and the side surfaces of the protective layer 50.

The acoustic module 30 may also be called an ultrasonic transducer. Various ultrasonic transducers such as a magnetostrictive ultrasonic transducer using a magnetostrictive effect of a magnetic material, a capacitive micromachined ultrasonic transducer, which transmits and receives ultrasonic waves using vibration of hundreds or thousands of micromachined thin films, and a piezoelectric ultrasonic transducer using a piezoelectric effect of a piezoelectric material, may be used. In the following description, a piezoelectric ultrasonic transducer will be described by way of example of the transducer.

A phenomenon in which a voltage is generated when mechanical pressure is applied to a predetermined object, and a phenomenon in which mechanical deformation occurs when a voltage is applied are referred to as piezoelectric effect and inverse piezoelectric effect, respectively. A material having these effects may be referred to as a piezoelectric material. That is, a piezoelectric material may be a material that converts electric energy into mechanical vibration energy, and converts mechanical vibration energy into electric energy.

The ultrasonic probe 10 may include the piezoelectric layer 30 formed of a piezoelectric material that converts an electric signal into mechanical vibration energy thereby generating an ultrasonic wave.

The piezoelectric material constituting the piezoelectric layer 30 may include a ceramic of lead zirconate titanate PZT, a PZMT single crystal formed of a solid solution of lead magnesium niobate and lead titanate or a PZNT single crystal formed of a solid solution of lead zinc niobate and lead titanate. Various other materials may be used to form the piezoelectric layer 30 to convert electric signals into mechanical vibrations.

In addition, the piezoelectric layer 30 may have a single-layered or multi-layered stack structure. In general, a piezoelectric layer 30 having a stack structure may more efficiently control impedance and voltage, thereby obtaining high sensitivity, high energy conversion efficiency, and smooth spectrum. In addition, the piezoelectric layer 30 may have various structures to improve performance of the piezoelectric layer 30.

The backing layer 40 is disposed on the bottom surface of the piezoelectric layer 30 and absorbs ultrasonic waves, which are generated in the piezoelectric layer 30 and proceed backward, so as to prevent the ultrasonic waves from proceeding backward from the piezoelectric layer 30. Accordingly, the backing layer 40 may prevent image distortion. The backing layer 40 may include a plurality of layers in order to improve attenuating or blocking effects of ultrasonic waves. In addition, various other structures may also be applied to the backing layer 40 to improve attenuating or blocking effects of ultrasonic waves.

The matching layer 20 may be disposed on the top surface of the piezoelectric layer 30. The matching layer 20 reduces difference of acoustic impedance between the piezoelectric layer 30 and the object, thereby matching acoustic impedance of the piezoelectric layer 30 and that of the object. Thus, the matching layer 20 may efficiently transmit ultrasonic waves generated by the piezoelectric layer 30 to the object. To this end, the matching layer 20 may have a median between the acoustic impedance of the piezoelectric layer 30 and that of the object.

The matching layer 20 may be formed of glass or resin. In addition, various other materials may also be used to form the matching layer 20 in order to match the acoustic impedance of the piezoelectric layer 30 and that of the object.

The matching layer 20 may include a plurality of layers such that the acoustic impedance is changed in a stepwise manner from the acoustic impedance of the piezoelectric layer 30 to that of the object. Alternatively, a plurality of different materials may be used to form the plurality of layers of the matching layer 20. In addition, the matching layer 20 may have various structures to change the acoustic impedance in a stepwise manner.

In addition, the piezoelectric layer 30 and the matching layer 20 may be processed in a 2D matrix array or a one-dimensional (1D) array by a dicing process.

The protective layer 50 may be installed to cover the top surface of the matching layer 20 and portions of the side surfaces of the acoustic module 100. The protective layer 50 may include a chemical shield capable of protecting internal parts from water and chemicals used during decontamination by coating or depositing a conductive material on a surface of a film having moisture resistance and chemical resistance. The chemical shield may be formed by applying a polymer film on the top surface of the matching layer 20 and portions of the side surfaces of the acoustic module 100 by parylene-coating. The chemical shield may also be formed by applying a section sputter to a polymer film.

In addition, the protective layer 50 may include a radio frequency (RF) shield to block outflow of radio frequency components, which may be generated in the piezoelectric layer 30, and inflow of external radio frequency components. In addition, the protective layer 50 may have various other configurations to block inflow and outflow of radio frequency components.

The lens layer 60 may be installed to cover the top surface and the side surfaces of the protective layer 50. The lens layer 60 may be formed of a low attenuation material in order to prevent attenuation of ultrasonic signals generated by the piezoelectric layer 30. For example, a low viscosity epoxy resin such as DER322 or an epoxy such as DEH24 may be used. Various other materials may also be used to form the lens layer 60 to prevent attenuation of ultrasonic signals. As such, sensitivity of the ultrasonic signals may be improved by preparing the lens layer 60 using a low attenuation material.

In addition, since the lens layer 60 is installed to cover portions of kerfs of the acoustic module 100 that constitute the side surfaces of the acoustic module 100, crosstalk may be reduced.

Hereinafter, an arrangement of a plurality of transducer modules 13 according to an embodiment of the present invention will be described with reference of FIG. 3.

Each of the plurality of transducer modules 13 may include a controller 12 and an acoustic module 11 disposed on the top surface of the controller 12.

The plurality of transducer modules 13 connected to the array may be arranged in various methods according to a region to be diagnosed, a purpose of use of the ultrasonic probe 10, and other grounds. For example, the transducer modules 13 may be arranged in a matrix, linear, convex, phased, or concave array.

Figure 3:
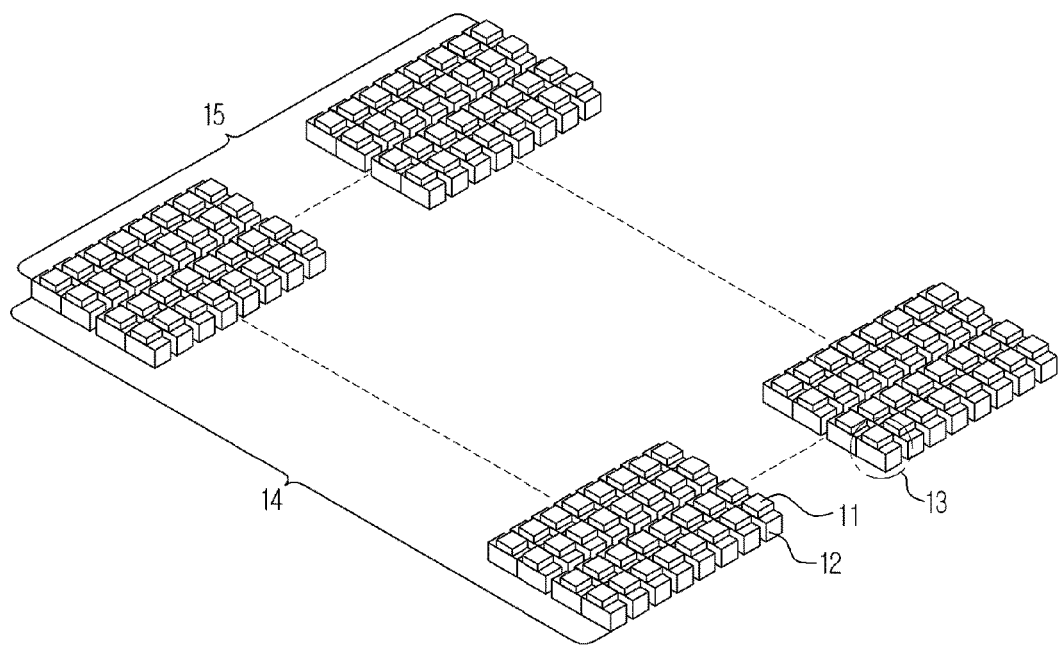
FIG. 3 is a perspective view illustrating a two-dimensional matrix array of transducer modules according to an embodiment of the present invention.

FIG. 3 illustrates that the transducer modules 13 are arranged in a 2D matrix form.

For example, 144 transducer modules 13 may be arranged along a horizontal axis 14 of the array, and 72 transducer modules 13 may be arranged along a vertical axis 15 of the array. Thus, the transducer modules 13 may be arranged in a 144×72 matrix, as a 2D matrix, and 10368 transducer modules 13 in total may be arranged.

However, the number of the transducer modules 13 in the 2D matrix form is not limited by the 144×72 matrix, and the transducer modules 13 may be arranged in various methods and the number thereof may vary according to the region to be diagnosed, the purpose of use of the ultrasonic probe 10, and any other grounds.

Hereinafter, an ultrasonic probe in which a central backing material layer of a second backing layer is fixed according to an embodiment of the present invention will be described with reference to FIG. 4.

Figure 4:
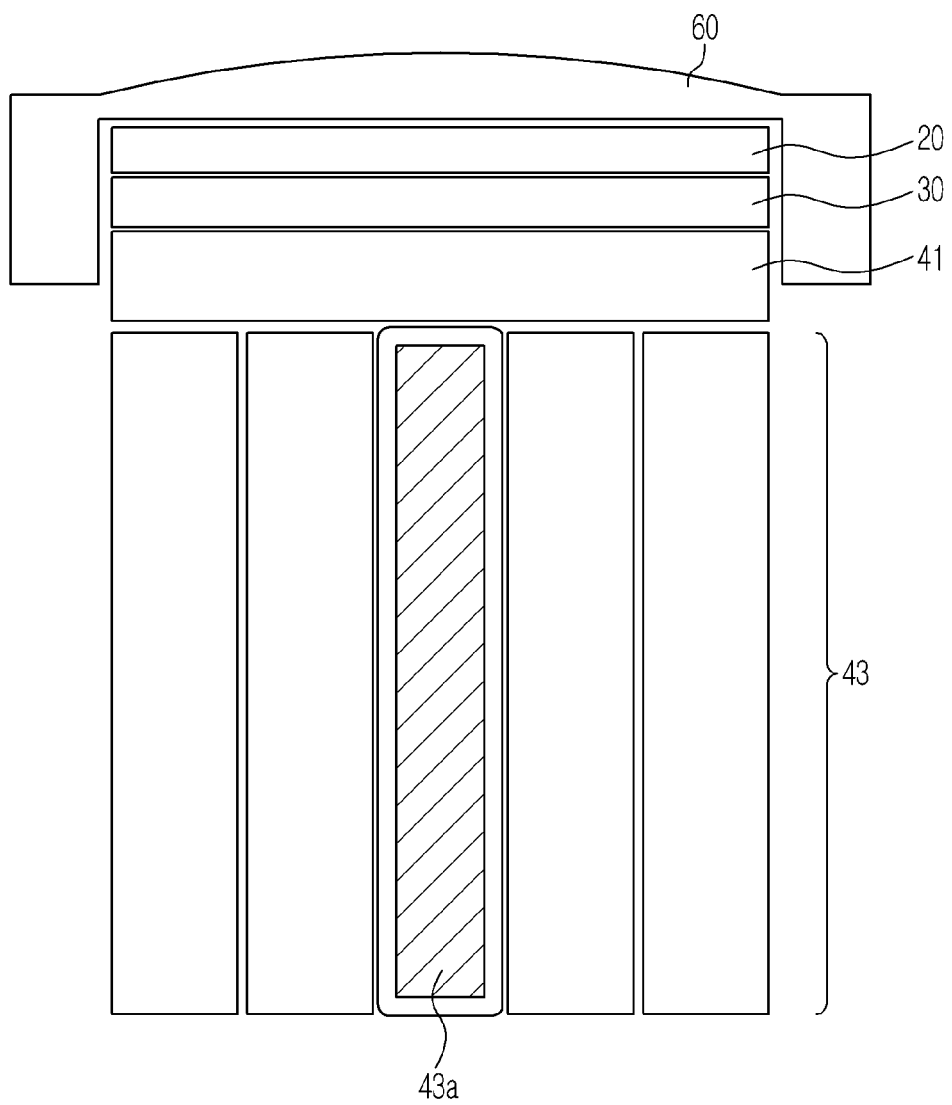
FIG. 4 is a cross-sectional view illustrating an ultrasonic probe in which a central backing material layer among a plurality of backing material layers of a second backing layer is fixed to a first backing layer to prevent horizontal movement of the central backing material layer according to an embodiment of the present invention.

FIG. 4 illustrates a cross-section of an ultrasonic probe in which a central backing material layer among a plurality of backing material layers of a second backing layer 43 is fixed to a first backing layer 41 to prevent horizontal movement of the central backing layer.

The ultrasonic probe may include a matching layer 20, a piezoelectric layer 30, a lens layer 60, and a backing layer.

The matching layer 20 may match acoustic impedance of the piezoelectric layer 30 to that of an object to be diagnosed, thereby efficiently transmitting ultrasonic waves generated by the piezoelectric layer 30 to the object, The piezoelectric layer 30 may transmit ultrasonic waves by converting electric energy into mechanical vibration energy or receive ultrasonic waves by converting mechanical vibration energy into electric energy. In addition, the lens layer 60 may prevent attenuation of ultrasonic signals generated by the piezoelectric layer 30.

In addition, a focal zone of the ultrasonic probe is adjusted by changing curvatures of the matching layer 20, the piezoelectric layer 30, and the lens layer 60 in accordance with a change in a curvature of the backing layer controlled by a backing layer adjusting unit. Thus, the matching layer 20, the piezoelectric layer 30, and the lens layer 60 may be formed of flexible materials to be bent according to the change of the curvature of the backing layer.

The backing layer may block the ultrasonic waves and vibrations generated in the piezoelectric layer 30 not to proceed backward, and may attenuate vibrations generated in the piezoelectric layer 30, and the like. The backing layer may be disposed on the bottom surface of the piezoelectric layer 30 and may include a first backing layer 41 and a second backing layer 43.

The first backing layer 41 may be disposed on the bottom surface of the piezoelectric layer 30 parallel to the piezoelectric layer 30. In addition, the first backing layer 41 may be formed of epoxy, ceramic, metal, or the like, e.g., in powder form, to prevent backward transmission of the ultrasonic waves and vibrations generated in the piezoelectric layer 30. Alternatively, powders of epoxy, ceramic, and metal may be mixed in a predetermined ratio to synthesize the first backing layer 41. In addition, various other materials to attenuate the ultrasonic waves and vibrations proceeding backward may also be used to form the first backing layer 41.

The second backing layer 43 may include a plurality of flat plate-shaped backing material layers stacked perpendicularly to the first backing layer 41 and parallel to each other.

In addition, the plurality of backing material layers may be spaced apart from each other by a predetermined interval to change the curvature of the first backing layer 41.

Furthermore, a central backing material layer 43a among the plurality of backing material layers of the second backing layer 43 may be fixed to the first backing layer 41 not to move horizontally, such that the central backing material layer 43a may be used as a reference when the second backing layer adjusting unit changes the curvature of the first backing layer 41.

In addition, the second backing layer 43 may have various other structures to change the curvature of the first backing layer 41.

A material used to form the second backing layer 43 may be the same as or different from that of the first backing layer 41.

Hereinafter, methods of changing a curvature of the second backing layer 43 having a fixed central backing material layer using second backing layer adjusting units 71a will be described with reference to FIGS. 5A to 6B.

Figure 5A:
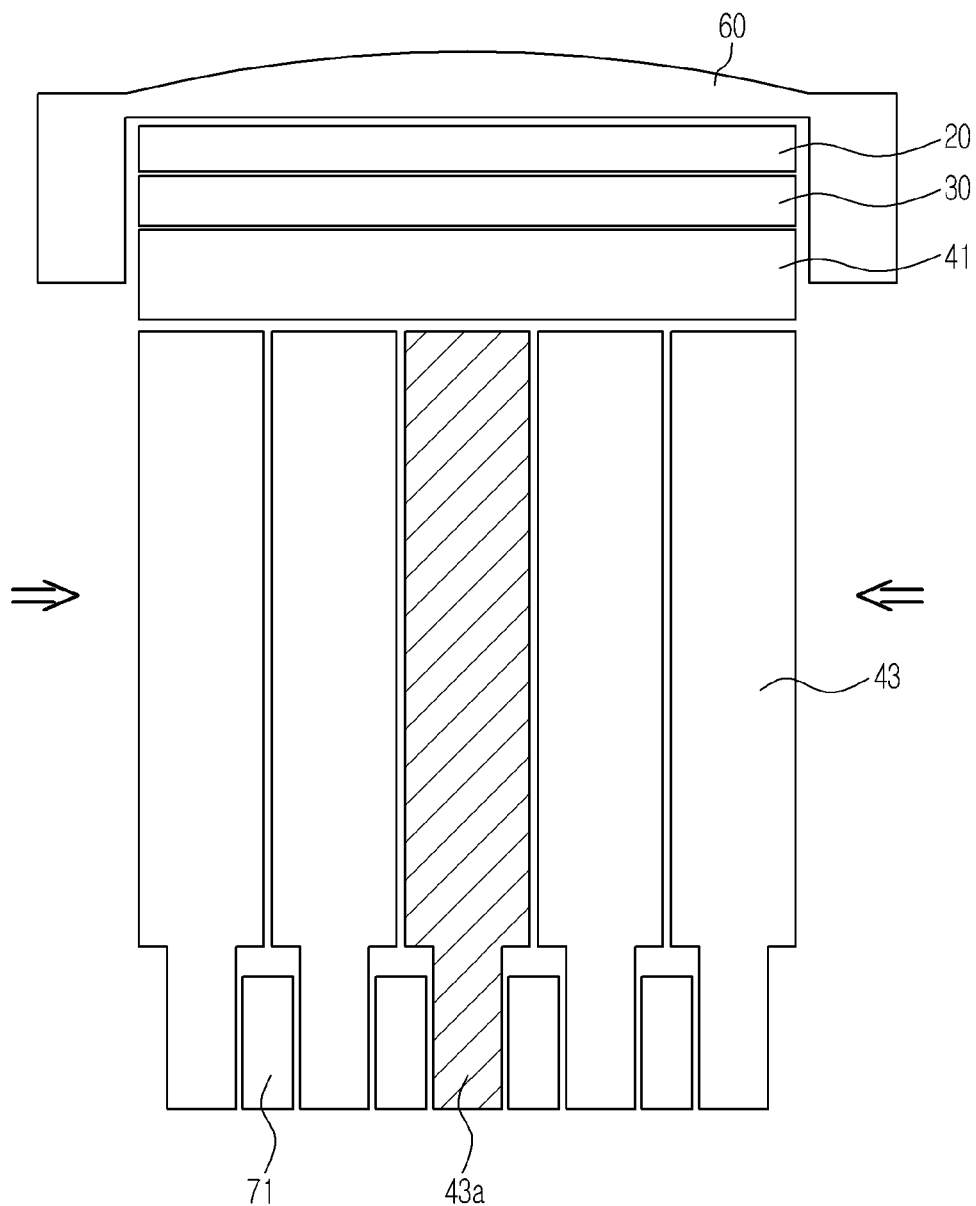
FIG. 5A is a conceptual diagram illustrating a method of decreasing a curvature of a second backing layer of an ultrasonic probe in which a central backing material layer of the second backing layer is fixed to a first backing layer, without vertical movement of second backing layer adjusting units according to an embodiment of the present invention.

FIG. 5A is a conceptual diagram illustrating a method of decreasing a curvature of a second backing layer 43 of an ultrasonic probe in which a central backing material layer of the second backing layer 43 is fixed to a first backing layer 41, without vertical movement of the second backing layer adjusting units 71. FIG. 5A is a conceptual diagram illustrating a method of decreasing the curvature of the second backing layer 43 of an ultrasonic probe in which a central backing material layer of the second backing layer 43 is fixed to the first backing layer 41, without vertical movement of the second backing layer adjusting units 71.

Figure 5B:
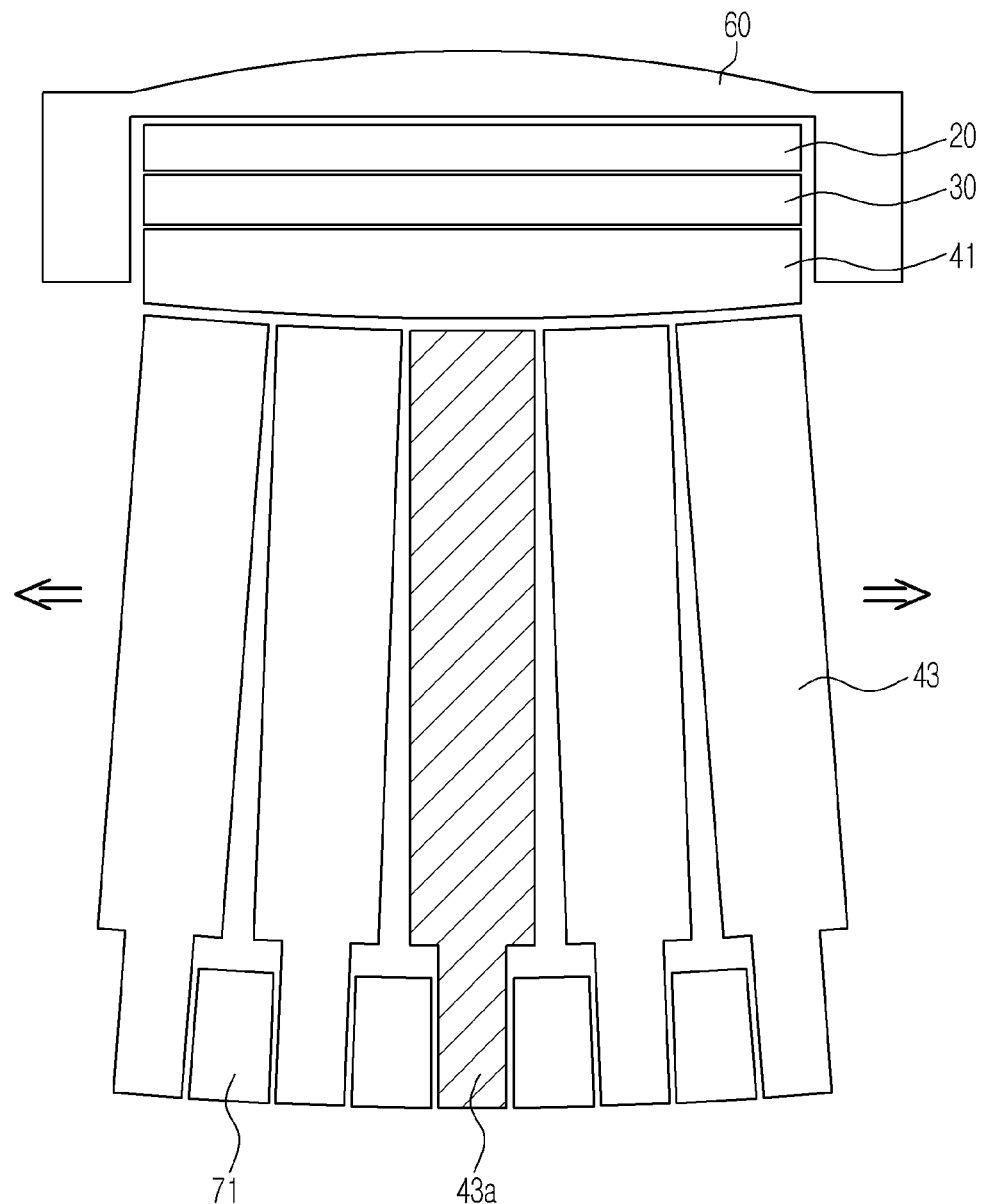
FIG. 5B is a conceptual diagram illustrating a method of increasing a curvature of a second backing layer of an ultrasonic probe in which a central backing material layer of the second backing layer is fixed to a first backing layer, without vertical movement of second backing layer adjusting units according to an embodiment of the present invention.

As illustrated in FIGS. 5A and 5B, an upper portion, adjacent to the first backing layer 41, of each of the backing material layers of the second backing layer 43 may have a greater thickness than a lower portion thereof such that each of the second backing layer adjusting units 71, which do not move vertically, is provided at the lower portion of the backing material layer.

The second backing layer adjusting units 71, which do not vertically move, may be disposed between the lower portions of the backing material layers. The second backing layer adjusting units 71 may adjust a lower width of the second backing layer 43 by respectively controlling only the widths of the second backing layer adjusting units 71 without vertical movement thereof.

The shape, location, and operation principle of the second backing layer adjusting units 71 will be described later.

As illustrated in FIG. 5A, the ultrasonic probe may have a wider focal zone by horizontally contracting the second backing layer adjusting units 71. When the second backing layer adjusting units 71 contract horizontally, the lower width of the second backing layer 43 is reduced, so that the plurality of backing material layers are disposed parallel to each other. Thus, as the second backing layer adjusting units 71a reduces the lower width of the second backing layer 43, the curvature of the first backing layer 41 is decreased, thereby enlarging the focal zone of the ultrasonic probe.

As illustrated in FIG. 5B, the ultrasonic probe may have a narrower focal zone by horizontally expanding the second backing layer adjusting units 71. When the second backing layer adjusting units 71 expand horizontally, the lower width of the second backing layer 43 is increased, so that the plurality of backing material layers except for the central backing material layer are slanted. Thus, as the second backing layer adjusting units 71 increase the lower width of the second backing layer 43, the curvature of the first backing layer 41 is increased, thereby narrowing the focal zone of the ultrasonic probe.

Figure 6A:
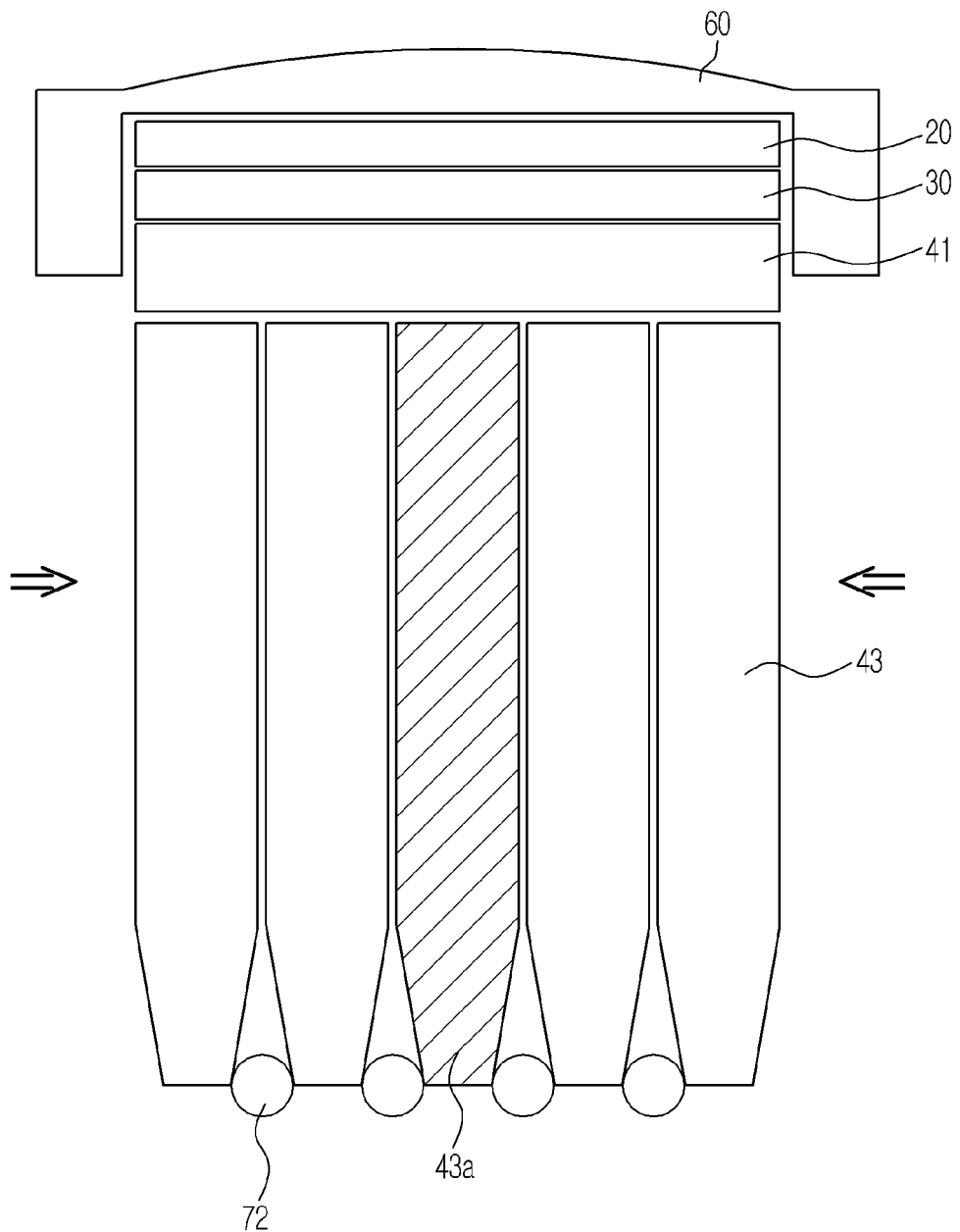
FIG. 6A is a conceptual diagram illustrating a method of decreasing a curvature of a second backing layer of an ultrasonic probe in which a central backing material layer of the second backing layer is fixed to a first backing layer, through vertical movement of second backing layer adjusting units according to an embodiment of the present invention.
Figure 6B:
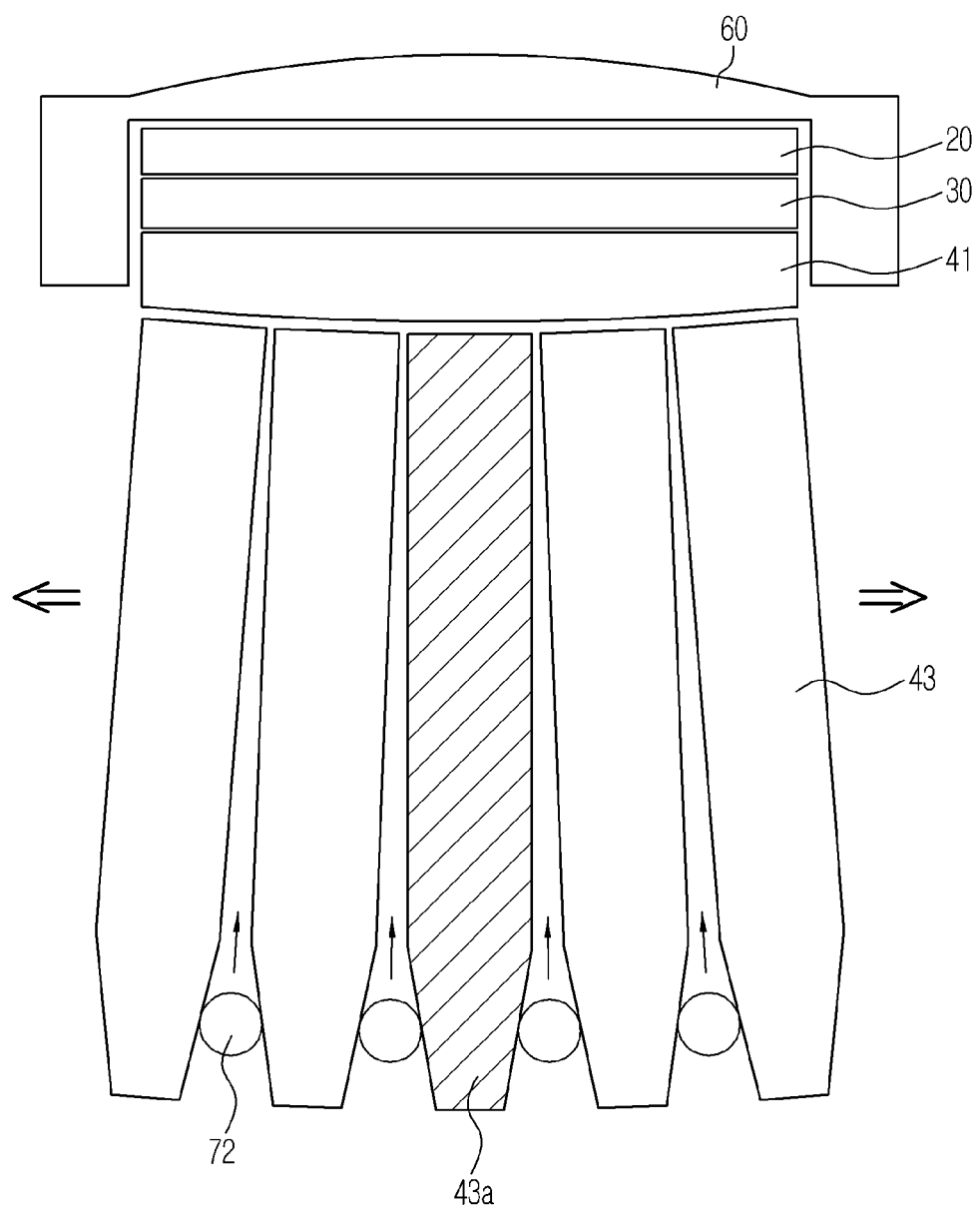
FIG. 6B is a conceptual diagram illustrating a method of increasing a curvature of a second backing layer of an ultrasonic probe in which a central backing material layer of the second backing layer is fixed to a first backing layer, through vertical movement of second backing layer adjusting units according to an embodiment of the present invention.

FIG. 6A is a conceptual diagram illustrating a method of decreasing a curvature of a second backing layer 43 of an ultrasonic probe in which a central backing material layer of the second backing layer 43 is fixed to a first backing layer 41, by vertically moving second backing layer adjusting units 72. FIG. 6B is a conceptual diagram illustrating a method of increasing the curvature of the second backing layer 43 of the ultrasonic probe in which the central backing material layer of the second backing layer 43 is fixed to the first backing layer 41, by vertically moving the second backing layer adjusting units 72.

As illustrated in FIGS. 6A and 6B, an upper portion, adjacent to the first backing layer 41, of each of the backing material layers of the second backing layer 43 may have a greater thickness than a lower portion thereof such that the second backing layer adjusting units 72, which move vertically, are provided between the lower portions of the backing material layers. In addition, the lower portions of the backing material layers may have a slope with a predetermined angle or a gently curved surface so as to facilitate vertical movement of the second backing layer adjusting units 72.

The second backing layer adjusting units 72 may have a circular shape suitable for vertical movement along the backing material layers of the second backing layer 43 having the slopes or gently curved surfaces. In addition, the second backing layer adjusting units 72 may also have various other shapes suitable for vertical movement along the slopes or gently curved surfaces of the backing material layers.

The second backing layer adjusting units 72, which move vertically, may be disposed between the lower portions of the backing material layers. In addition, the second backing layer adjusting units 72 may control the lower width of the second backing layer 43 via only vertical movement without adjusting the width of each of the second backing layer adjusting units 72.

The shape, location, and operation principle of the second backing layer adjusting units 72 will be described later.

As illustrated in FIG. 6A, the ultrasonic probe may have a wider focal zone as the second backing layer adjusting units 72 move downward to lower portions of the backing material layers. When the second backing layer adjusting units 72 move downward to the lower portions of the backing material layers, the lower width of the second backing layer 43 is reduced, so that the plurality of backing material layers are disposed parallel to each other. Thus, as the second backing layer adjusting units 72 move downward to the lower portions of the backing material layers, the curvature of the first backing layer 41 is decreased, thereby enlarging the focal zone of the ultrasonic probe.

As illustrated in FIG. 6B, the ultrasonic probe may have a narrower focal zone as the second backing layer adjusting units 72 move upward to upper portions of the backing material layers. When the second backing layer adjusting units 72 move upward to upper portions of the backing material layers, the lower width of the second backing layer 43 is increased, so that the plurality of backing material layers except for the central backing material layer 43a are slanted. Thus, as the second backing layer adjusting units 72 move upward to the upper portions of the backing material layers, the curvature of the first backing layer 41 is increased, thereby narrowing the focal zone of the ultrasonic probe.

Hereinafter, an ultrasonic probe including fixing units 42a disposed at both sides of the second backing layer 43 to fix a plurality of backing material layers according to an embodiment of the present invention will be described with reference to FIG. 7.

Figure 7:
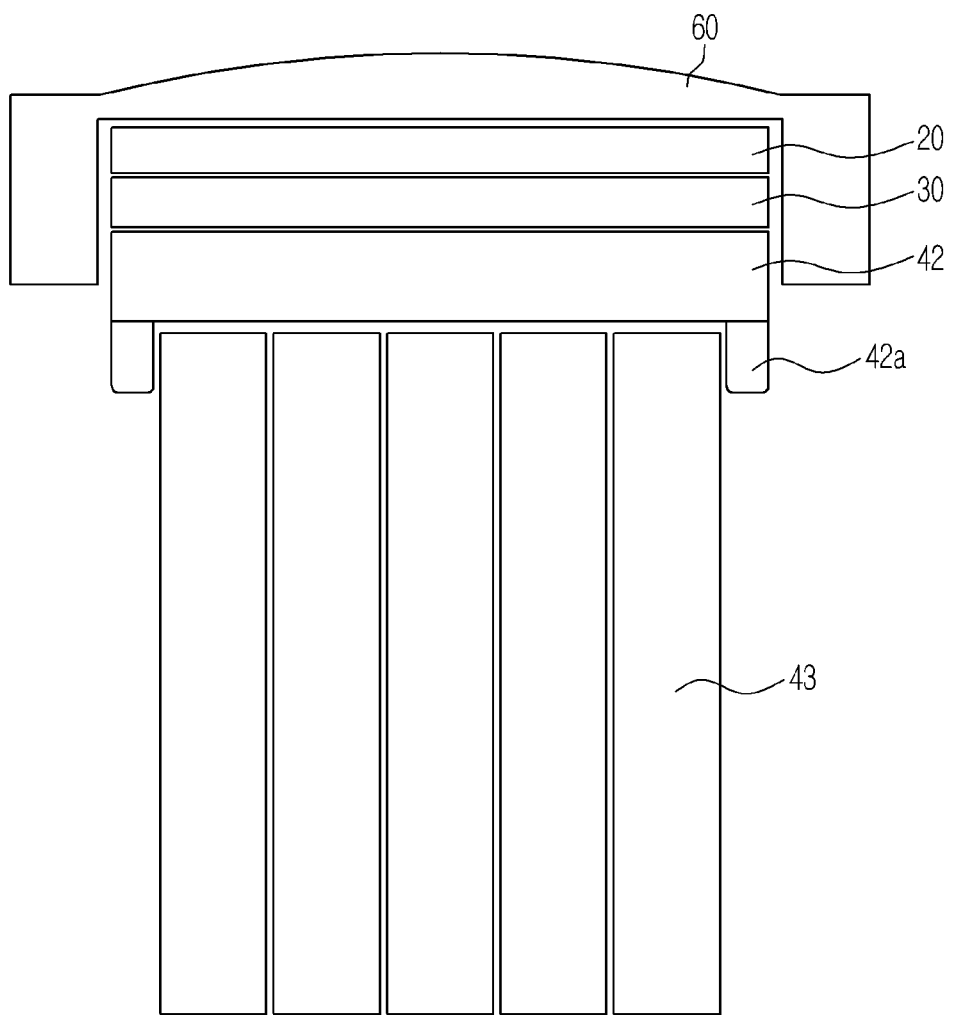
FIG. 7 is a cross-sectional view illustrating an ultrasonic probe in which a plurality of backing material layers of a second backing layer are fixed using fixing units disposed at both sides of the backing material layers according to an embodiment of the present invention.

FIG. 7 is a cross-sectional view illustrating an ultrasonic probe in which a plurality of backing material layers of a second backing layer 43 are fixed using fixing units 42a disposed at both sides of the backing material layers.

The ultrasonic probe may include a matching layer 20, a piezoelectric layer 30, a lens layer 60, and a backing layer. The backing layer may include a first backing layer 42 and a second backing layer 43.

Functions and shapes of the matching layer 20, the piezoelectric layer 30, the lens layer 60, and the second backing layer 43 may be the same as or different from those of the aforementioned ultrasonic probe in which the central backing material layer among the plurality of backing material layers of the second backing layer 43 is fixed to the first backing layer 42 not to move horizontally.

The first backing layer 42 may include fixing units 42a at both sides of the second backing layer 43 to fix upper portions of a plurality of backing material layers. Particularly, the first backing layer 42 may include the fixing units 42a such that only intervals between lower portions of the plurality of backing material layers are increased, and intervals between upper portions of the backing material layers are constantly maintained using the second backing layer adjusting units 71a, which do not move vertically, or the second backing layer adjusting units 72, which move vertically. In addition, the first backing layer 42 may also have various other shapes to adjust only intervals between lower portions of the backing material layers.

A material used to form the fixing units 42a may be the same as or different from that used to form the first backing layer 42 of the ultrasonic probe in which the central backing material layer among the plurality of backing material layers of the second backing layer 43 is fixed to the first backing layer 42 to prevent horizontal movement of the central backing material and maintain ultrasonic wave absorbing performance.

Hereinafter, methods of changing a curvature of a second backing layer 43 of an ultrasonic probe including fixing units 42a and second backing layer adjusting units 71, 72 will be described with reference to FIGS. 8A to 9B.

Figure 8A:
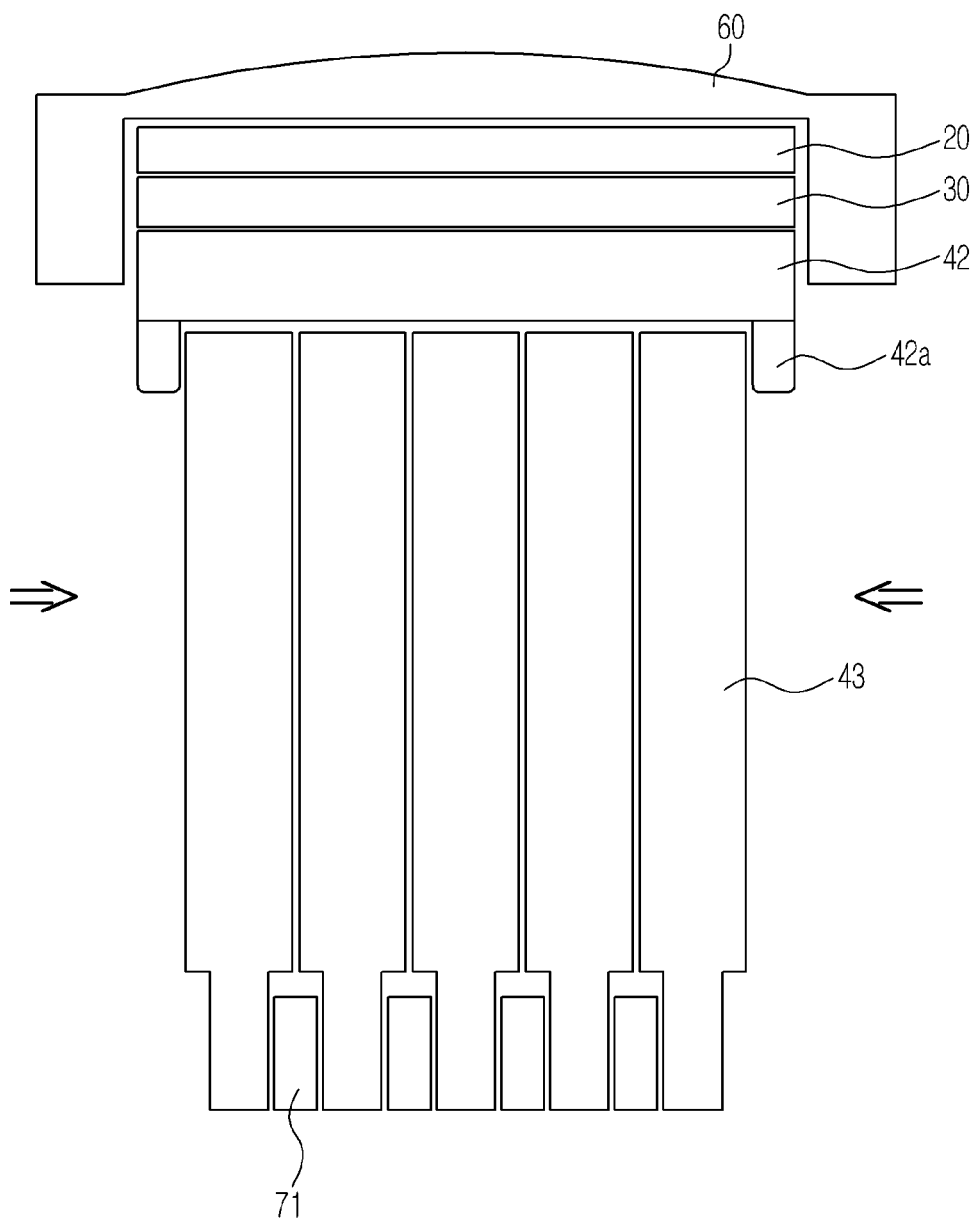
FIG. 8A is a conceptual diagram illustrating a method of decreasing a curvature of a second backing layer of an ultrasonic probe in which fixing units fix a plurality of backing material layers of the second backing layer, without vertical movement of second backing layer adjusting units according to an embodiment of the present invention.
Figure 8B:
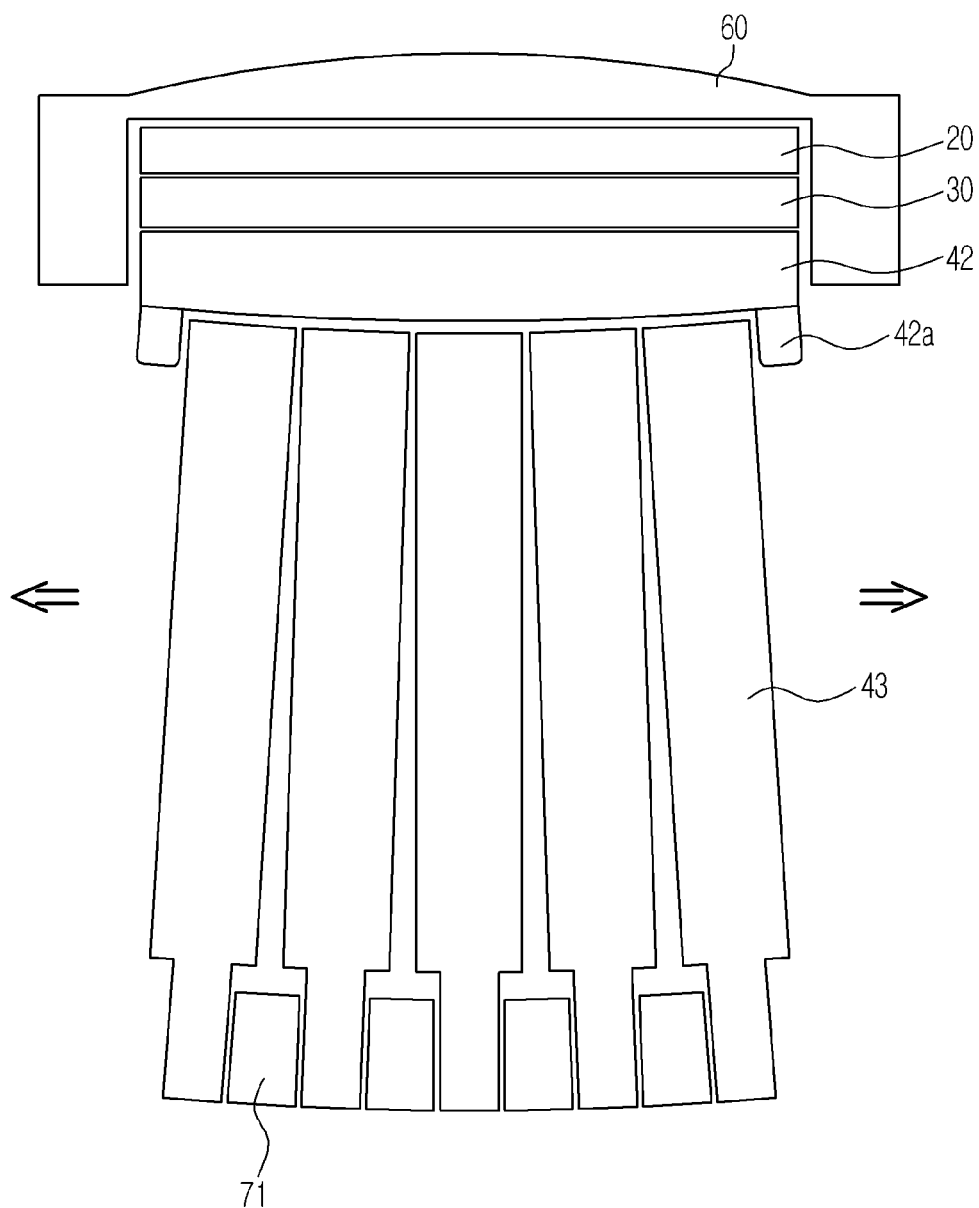
FIG. 8B is a conceptual diagram illustrating a method of increasing a curvature of a second backing layer of an ultrasonic probe in which fixing units fix a plurality of backing material layers of the second backing layer, without vertical movement of second backing layer adjusting units according to an embodiment of the present invention.

FIG. 8A is a conceptual diagram illustrating a method of decreasing a curvature of a second backing layer 43 of an ultrasonic probe in which fixing units 42a fix a plurality of backing material layers of the second backing layer 43, without vertical movement of second backing layer adjusting units 71. FIG. 8B is a conceptual diagram illustrating a method of increasing the curvature of the second backing layer 43 of the ultrasonic probe in which the fixing units 42a fix the plurality of backing material layers of the second backing layer 43, without vertical movement of the second backing layer adjusting units 71a.

As illustrated in FIGS. 8A and 8B, an upper portion, adjacent to the first backing layer 42, of each of the backing material layers of the second backing layer 43 may have a greater thickness than a lower portion thereof such that the second backing layer adjusting units 71, which does not move vertically, are provided between the lower portions of the backing material layers.

The second backing layer adjusting units 71, which do not move vertically, may be disposed between the lower portions of the backing material layers. The second backing layer adjusting units 71 may adjust a lower width of the second backing layer 43 by controlling only a width of each of the second backing layer adjusting units 71 without vertical movement thereof.

The shape, location, and operation principle of the second backing layer adjusting units 71 will be described later.

As illustrated in FIG. 8A, the ultrasonic probe may have a wider focal zone by horizontally contracting the second backing layer adjusting units 71. When the second backing layer adjusting units 71 contract horizontally, the lower width of the second backing layer 43 is reduced, so that the plurality of backing material layers are disposed parallel to each other. Thus, as the second backing layer adjusting units 71 reduces the lower width of the second backing layer 43, the curvature of the first backing layer 42 is decreased, thereby enlarging the focal zone of the ultrasonic probe.

As illustrated in FIG. 8B, the ultrasonic probe may have a narrower focal zone by horizontally expanding the second backing layer adjusting units 71. When the second backing layer adjusting units 71 expand horizontally, the lower width of the second backing layer 43 is increased, so that the plurality of backing material layers except for the central backing material layer are slanted. Thus, as the second backing layer adjusting units 71 increases the lower width of the second backing layer 43, the curvature of the first backing layer 42 is increased, thereby narrowing the focal zone of the ultrasonic probe.

Figure 9A:
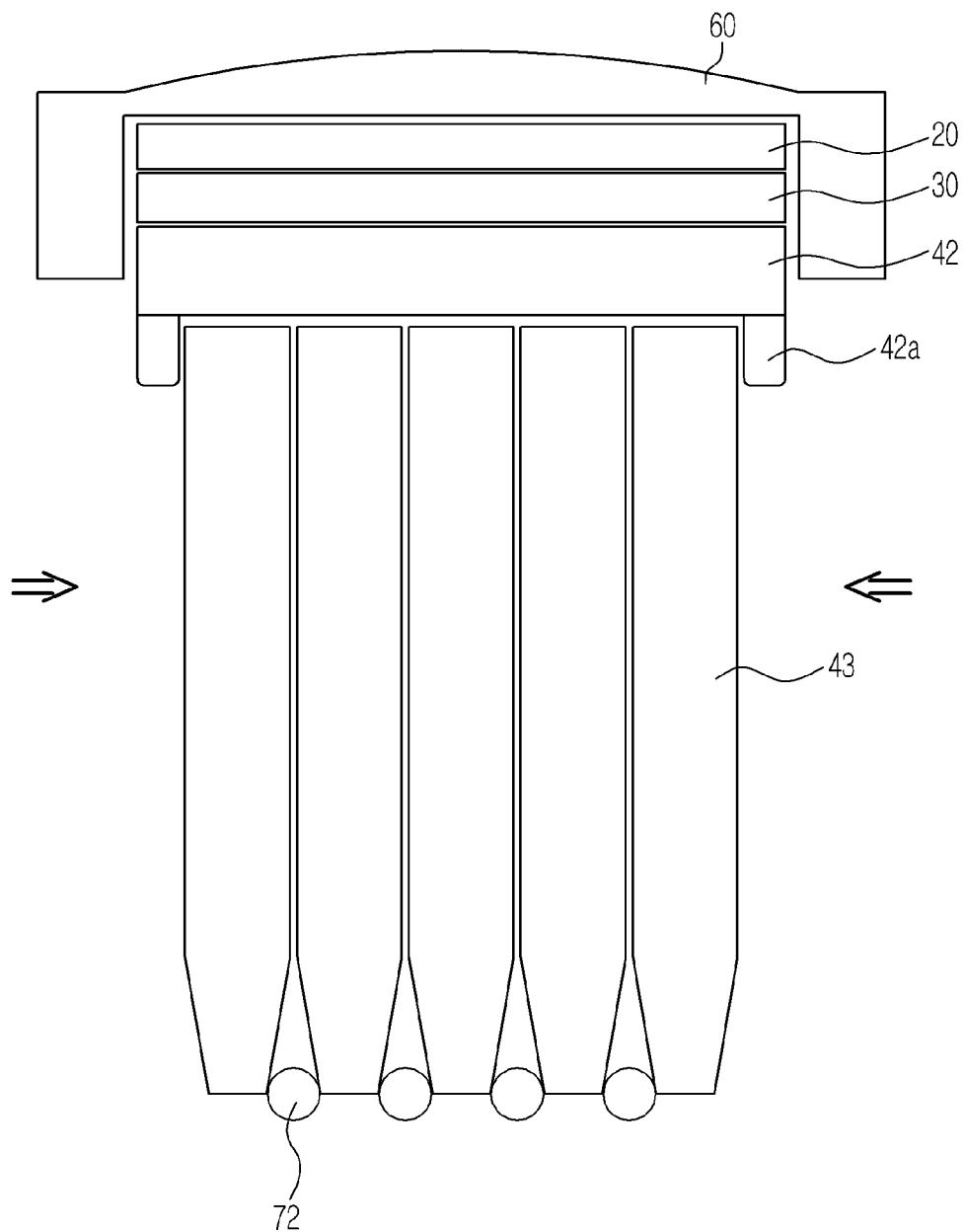
FIG. 9A is a conceptual diagram illustrating a method of decreasing a curvature of a second backing layer of an ultrasonic probe in which fixing units fix a plurality of backing material layers of the second backing layer, through vertical movement of second backing layer adjusting units according to an embodiment of the present invention.
Figure 9B:
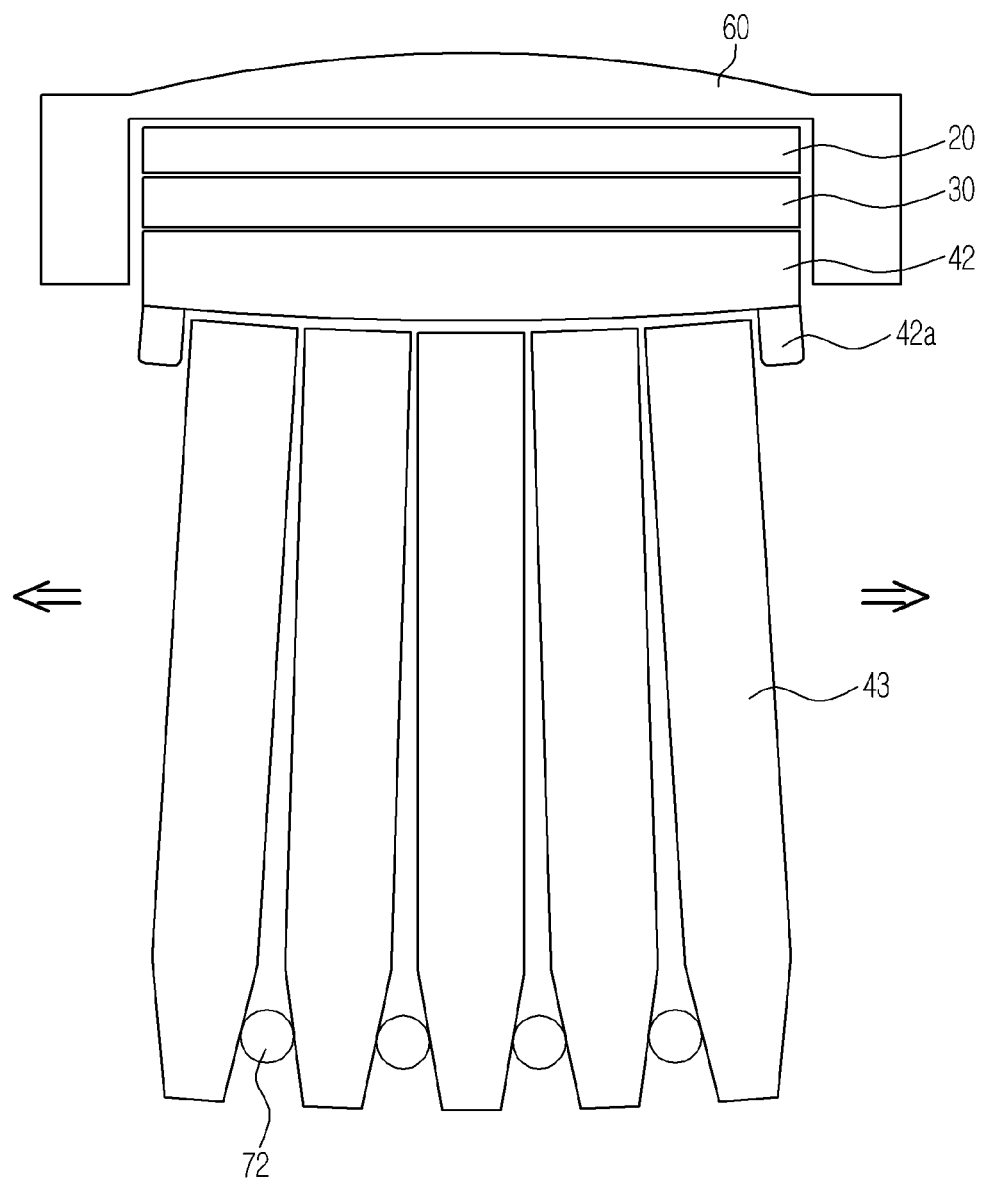
FIG. 9B is a conceptual diagram illustrating a method of increasing a curvature of a second backing layer of an ultrasonic probe in which fixing units fix a plurality of backing material layers of the second backing layer, through vertical movement of second backing layer adjusting units according to an embodiment of the present invention.

FIG. 9A is a conceptual diagram illustrating a method of decreasing a curvature of a second backing layer 43 of an ultrasonic probe in which fixing units 42a fix a plurality of backing material layers of the second backing layer 43 by vertically moving second backing layer adjusting units 72. FIG. 9B is a conceptual diagram illustrating a method of increasing the curvature of the second backing layer 43 of the ultrasonic probe in which the fixing units 42a fix the plurality of backing material layers of the second backing layer 43, by vertically moving the second backing layer adjusting units 72.

As illustrated in FIGS. 9A and 9B, an upper portion, adjacent to the first backing layer 42, of each of the backing material layers of the second backing layer 43 may have a greater thickness than a lower portion thereof such that the second backing layer adjusting units 72, which move vertically, are provided between the lower portions of the backing material layers. In addition, the lower portion of the backing material layer may have a slope with a predetermined angle or a gently curved surface so as to facilitate vertical movement of the second backing layer adjusting units 72.

The second backing layer adjusting units 72, which move vertically, may have a circular shape suitable for vertical movement along the backing material layers of the second backing layer 43 having the slopes or gently curved surfaces. In addition, the second backing layer adjusting units 72 may also have various other shapes suitable for vertical movement along the slopes or gently curved surfaces of the backing material layers.

The second backing layer adjusting units 72, which move vertically, may be disposed between the lower portions of the backing material layers. In addition, the second backing layer adjusting units 72 may control the lower width of the second backing layer 43 via only vertical movement without adjusting the width of each of the second backing layer adjusting units 72.

The shape, location, and operation principle of the second backing layer adjusting units 72 will be described later.

As illustrated in FIG. 9A, the ultrasonic probe may have a wider focal zone by vertically moving the second backing layer adjusting units 72 downward to the lower portions of the backing material layers. When the second backing layer adjusting units 72 move downward to lower portions of the backing material layers, the lower width of the second backing layer 43 is reduced, so that the plurality of backing material layers are disposed parallel to each other. Thus, as the second backing layer adjusting units 72 move downward to the lower portions of the backing material layers, the curvature of the first backing layer 42 is decreased, thereby enlarging the focal zone of the ultrasonic probe.

As illustrated in FIG. 9B, the ultrasonic probe may have a narrower focal zone by moving the second backing layer adjusting units 72 upward to upper portions of the backing material layers. When the second backing layer adjusting units 72 move upward to the upper portions of the backing material layers, the lower width of the second backing layer 43 is increased, so that the plurality of backing material layers except for the central backing material layer are slanted. Thus, as the second backing layer adjusting units 72 move upward to the upper portions of the backing material layers, the curvature of the first backing layer 42 is increased, thereby narrowing the focal zone of the ultrasonic probe.

Hereinafter, a method of changing a curvature of a first backing layer including barrier walls 44b using a first backing layer adjusting unit 71 according to an embodiment of the present invention will be described with reference to FIGS. 10A and 10B.

Figure 10A:
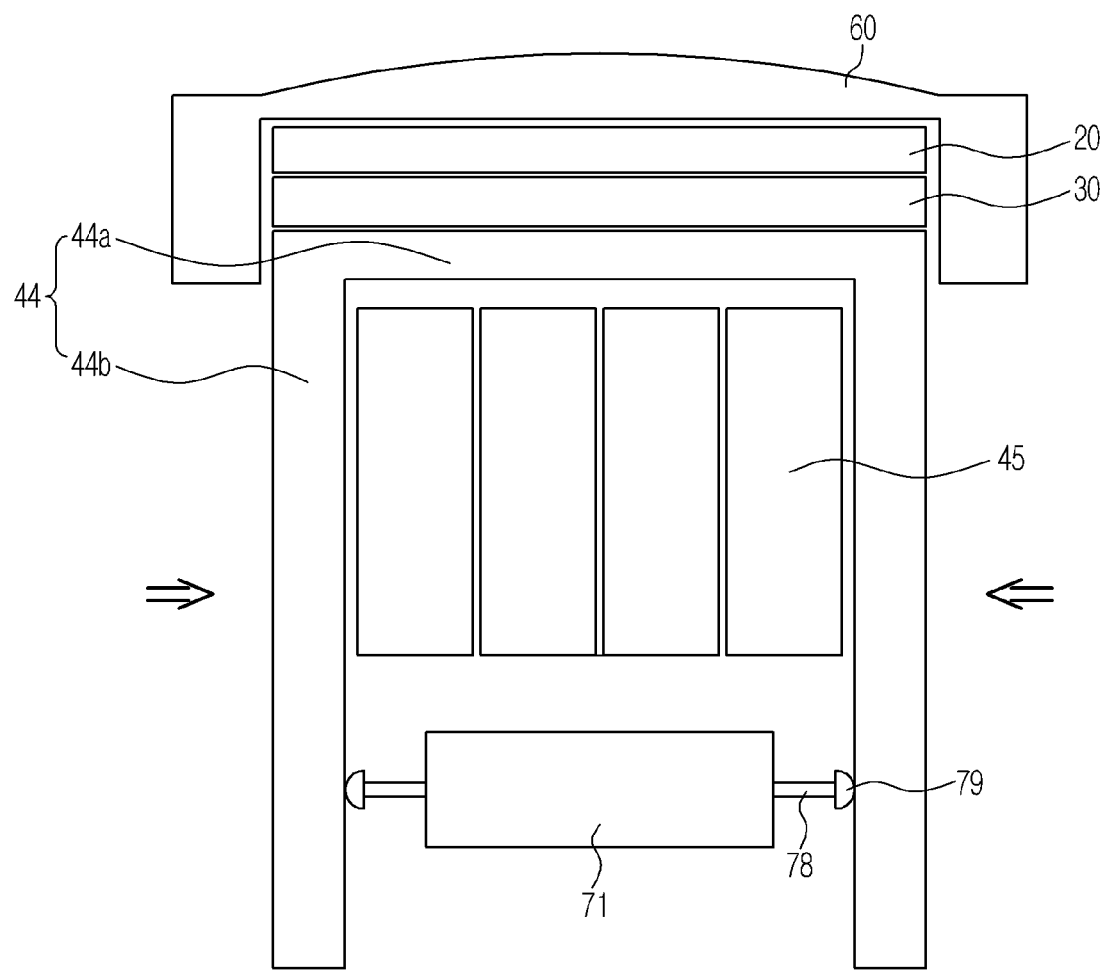
FIG. 10A is a conceptual diagram illustrating a method of decreasing a curvature of a first backing layer of an ultrasonic probe in which the first backing layer includes barrier walls, without vertical movement of a first backing layer adjusting unit according to an embodiment of the present invention.

FIG. 10A is a conceptual diagram illustrating a method of decreasing a curvature of a first backing layer of an ultrasonic probe in which a first backing layer 44 includes barrier walls 44b, without vertical movement of a first backing layer adjusting unit 71b. FIG. 10B is a conceptual diagram illustrating a method of increasing the curvature of the first backing layer 44 of the ultrasonic probe in which the first backing layer includes barrier walls 44b, without vertical movement of the first backing layer adjusting unit 71b.

As illustrated in FIGS. 10A and 10B, the ultrasonic probe may include a matching layer 20, a piezoelectric layer 30, a lens layer 60, and a backing layer. The backing layer may include a first backing layer 44 and a second backing layer 45.

Functions and shapes of the matching layer 20, the piezoelectric layer 30, the lens layer 60, and the second backing layer 45 may be the same as or different from those of the aforementioned ultrasonic probe in which a central backing material layer among the plurality of backing material layers of the second backing layer 45 is fixed to the first backing layer 44 not to move horizontally.

The first backing layer 44 may include a ceiling 44a and barrier walls 44b at both ends, each having a height greater than that of the second backing layer 45. Particularly, in the previous embodiment, a curvature of the first backing layer is changed by controlling intervals between lower portions of a plurality of backing material layers of the second backing layer 45, and then curvatures of the lens layer 60, the matching layer 20, and the piezoelectric layer 30 disposed on the top surface of the first backing layer are changed in accordance with the changed curvature of the first backing layer. Differently, according to the current embodiment, the curvature of the first backing layer 44 is changed by controlling an interval between lower portions of the barrier walls 44b of the first backing layer 44, and then the curvatures of the lens layer 60, the matching layer 20, and the piezoelectric layer 30 disposed on the top surface of the second backing layer 45 may be changed in accordance with the changed curvatures of the first backing layer 44. In addition, the first backing layer 44 may also have various other shapes to adjust the interval between the lower portions of the barrier walls 44b of the first backing layer 44.

A material used to form the barrier walls 44b of the first backing layer 44 may be the same as or different from a material used to form the first backing layer 44 of the ultrasonic probe in which the first backing layer adjusting unit 71b is fixed to the first backing layer 44 such that the first backing layer adjusting unit 71b directly controls the curvature of the first backing layer 44 and the barrier walls 44b maintain ability to absorb ultrasonic waves.

As illustrated in FIGS. 10A and 10B, the barrier walls 44b of the first backing layer 44 may respectively have a height greater than that of the second backing layer 45 such that the first backing layer adjusting unit 71b, which does not move vertically, is provided therebetween.

The first backing layer adjusting unit 71b, which does not move vertically, may be disposed in a space defined by the bottom surface of the plurality of backing material layers and the barrier walls 44b of the first backing layer 44. The first backing layer adjusting unit 71*a* may adjust the interval between lower portions of the barrier walls 44*b* by adjusting only the width of the first backing layer adjusting unit 71*a* without vertical movement.

The shape, location, and operation principle of the first backing layer adjusting unit 71*b*, which does not move vertically, will be described later.

As illustrated in FIG. 10A, the ultrasonic probe may have a wider focal zone by horizontally contracting the first backing layer adjusting unit 71*b*. When the first backing layer adjusting unit 71*b* contracts horizontally, the lower interval between the barrier walls 44*b* of the first backing layer 44 is reduced so that the barrier walls 44*b* of the first backing layer 44 are disposed parallel to each other. Thus, as the first backing layer adjusting unit 71*b* reduces the lower interval between the barrier walls 44*b* of the first backing layer 44, the curvature of the first backing layer 44 is decreased, thereby enlarging the focal zone of the ultrasonic probe.

As illustrated in FIG. 10B, the ultrasonic probe may have a narrower focal zone by horizontally expanding the first backing layer adjusting unit 71*b*. When the first backing layer adjusting unit 71*b* expands horizontally, the lower interval between the barrier walls 44*b* of the first backing layer 44 increases, and an upper interval between the barrier walls 44*b* of the first backing layer 44 is maintained since the upper portions of the barrier walls 44*b* are fixed to the ceiling 44*a*. Accordingly, the barrier walls 44*b* of the first backing layer 44 are slanted. Thus, as the first backing layer adjusting unit 71*b* increases the lower interval between the barrier walls 44*b* of the first backing layer 44, the curvature of the first backing layer 44 is increased, thereby narrowing the focal zone of the ultrasonic probe.

Hereinafter, displacements of the first backing layer 44 including the barrier walls 44*b* will be described with reference to FIGS. 11 and 12.

Figure 11:
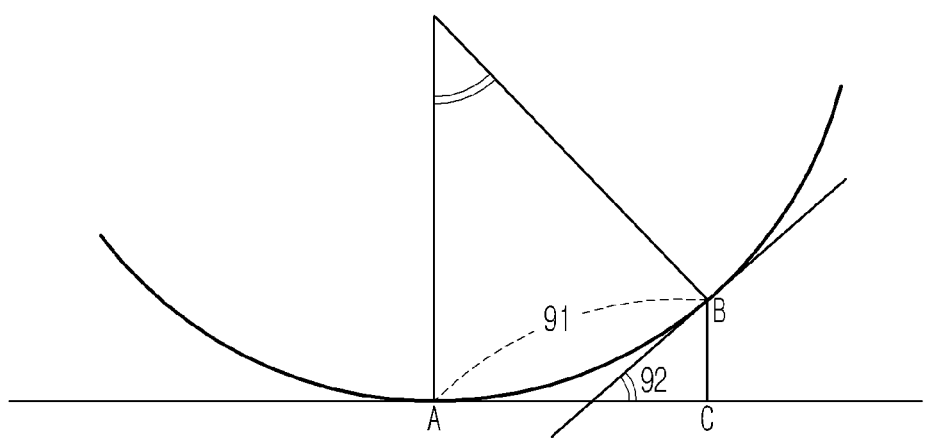
FIG. 11 is a conceptual diagram illustrating curvature, height, horizontal displacement, and Vertical displacement of a first backing layer including barrier walls according to an embodiment of the present invention.

FIG. 11 is a conceptual diagram illustrating curvature 90, height 93, horizontal displacement 95, and Vertical displacement 94 of the first backing layer 44 including the barrier walls 44*b*. FIG. 12 is a conceptual diagram illustrating curvature 90.

The curvature 90 is a variable indicating the degree of bending of a curved line or a curved surface. The curvature 90 is in inverse relationship with a curvature radius, which is a variable indicating a radius of an arc determined by using a small portion of a curve. The curvature 90 increases as the radius of curvature decreases.

Figure 12:
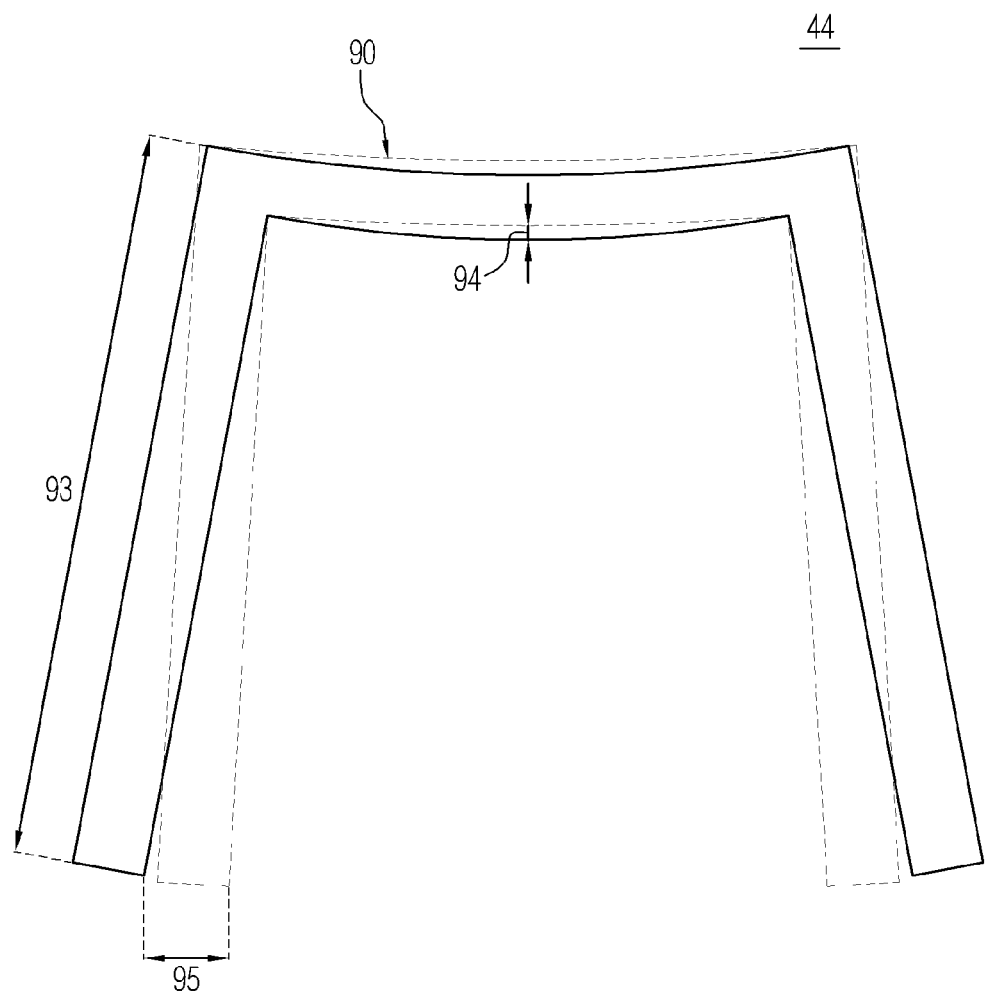
FIG. 12 is a conceptual diagram illustrating curvature according to an embodiment of the present invention.

Particularly, when a point on a curve moves from A to B as illustrated in FIG. 12, a variation of distance 91 there between may be defined as Δs, and a variation of exterior angle 92 between tangent lines of points A and B may be defined as Δθ. Hereinafter, a curvature 90(*k*) will be described by using Equation 1 below.

$$k = \lim_{\Delta s \to 0} \left| \frac{\Delta \theta}{\Delta s} \right| = \left| \frac{d\theta}{ds} \right|$$ Equation 1

The curvature 90(*k*) is a directional variation of Δθ, which is a variation of exterior angle 92 between tangential lines of points A and B. The curvature 90(*k*) may be an absolute value of Δθ/Δs, when Δs converges on 0. Alternatively, the curvature 90(*k*) may be a value acquired by differentiate θ, which is an exterior angle 92 between tangential lines of points A and B, with respect to s, as the distance 91.

Hereinafter, the curvature 90 described above with reference to FIG. 12, the height 93, the Vertical displacement 94, and the horizontal displacement 95 of the barrier walls 44*b* of the first backing layer 44 will be described.

Dashed lines of FIG. 11 indicate the shape of the first backing layer 44 including the barrier walls 44*b* when the lower interval between the barrier walls 44*b* of the first backing layer 44 is reduced by the first backing layer adjusting unit 71*b*. Solid lines of FIG. 11 indicate the first backing layer 44 including the barrier walls 44*b* when the lower interval between the barrier walls 44*b* of the first backing layer 44 is increased by the first backing layer adjusting unit 71*b*.

As illustrated in FIG. 11, the height 93 of the barrier walls 44*b* of the first backing layer 44 is a variable uncontrollable by the first backing layer adjusting unit 71*b*, and the curvature 90 of the first backing layer 44 is a variable controllable by the first backing layer adjusting unit 71*b*. As the lower interval between the barrier walls 44*b* decreases, the curvature 90 decreases. As the lower interval between the barrier walls 44*b* increases, the curvature 90 increases.

In addition, the Vertical displacement 94 is a variation of the ceiling 44*a* of the first backing layer 44 including the barrier walls 44*b* in the vertical direction when the lower interval between the barrier walls 44*b* of the first backing layer 44 is adjusted by the first backing layer adjusting unit 71*b*. The horizontal displacement 95 is a variation of the barrier walls 44*b* of the first backing layer 44 in the horizontal direction when the lower interval between the barrier walls 44*b* of the first backing layer 44 is adjusted by the first backing layer adjusting unit 71*b*.

TABLE 1

| Array of transducer module | Width of opening of transducer module [mm] | Height of barrier wall [mm] | Curvature [mm] | Vertical displacement [mm] | Horizontal displacement [mm] |
|---|---|---|---|---|---|
| Phased array | 14 | 10 | 65~90 | 0.105 | 0.303 |
| Linear array | 4 | 5 | 10~18 | 0.102 | 0.923 |
| | 5 | 5 | 10~18 | 0.089 | 1.180 |
| | 14 | 10 | 120~160 | 0.051 | 0.104 |

Table 1 shows the curvatures 90, the Vertical displacements 94, and the horizontal displacements 95 of the first backing layer 44 including the barrier walls 44*b* with respect to the width of an opening of the transducer module and the height 93 of the barrier walls 44*b* when the transducer modules are arranged in a phased or linear array.

The shape and characteristics of the ultrasonic probe are not limited by the variables listed in Table 1 and the arrangement of the transducer modules, and appropriate variables may be selected according to the lens layer 60, the matching layer 20, the piezoelectric layer 30, the backing layer, other components, regions to be diagnosed, and other grounds.

Hereinafter, backing layer adjusting units to change a curvature of a backing layer according to an embodiment of the present invention will be described with reference to FIGS. 13A to 15B.

Figure 13A:
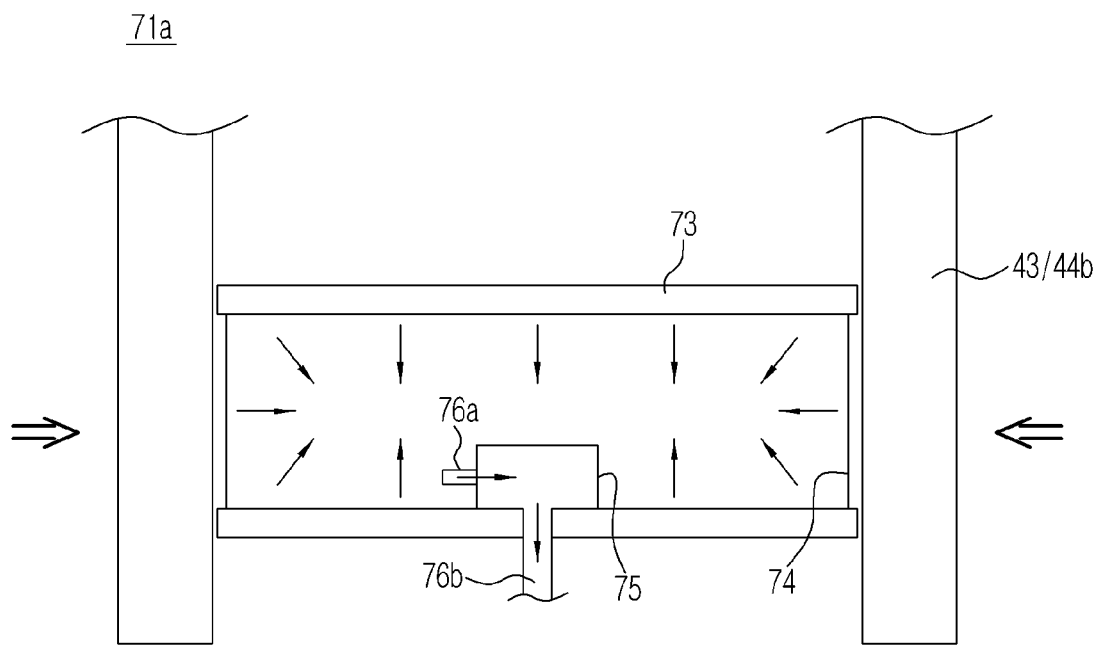
FIG. 13A is a conceptual diagram illustrating a method of decreasing a curvature of a backing layer without vertical movement of a backing layer adjusting unit including an actuator according to an embodiment of the present invention.
Figure 13B:
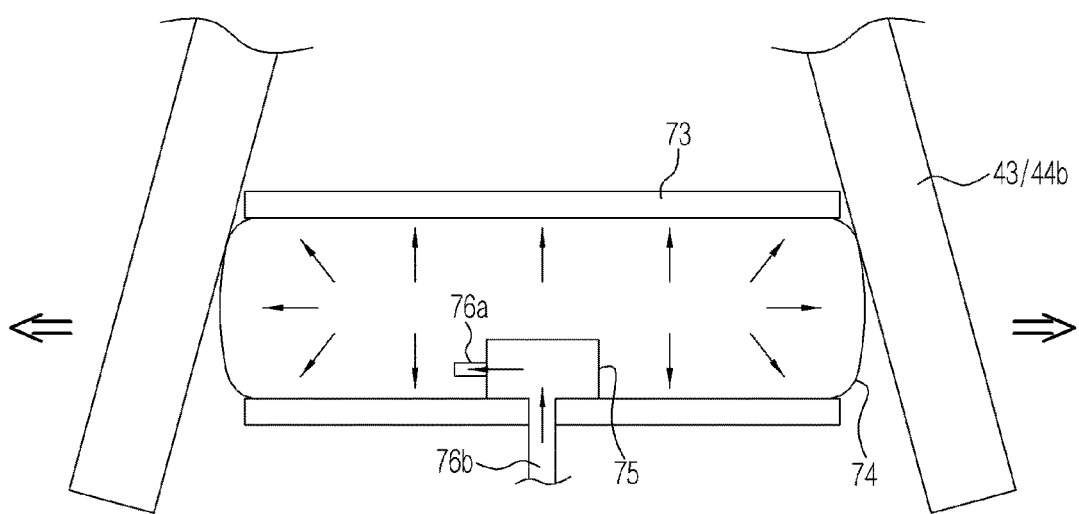
FIG. 13B is a conceptual diagram illustrating a method of increasing a curvature of a backing layer without vertical movement of a backing layer adjusting unit including an actuator according to an embodiment of the present invention.

FIG. 13A is a conceptual diagram illustrating a method of decreasing a curvature of a backing layer without vertical movement of a backing layer adjusting unit 71*a* including an actuator 75. FIG. 13B is a conceptual diagram illustrating a method of increasing the curvature of the backing layer without vertical movement of the backing layer adjusting unit 71a including the actuator 75.

The backing layer adjusting unit 71a including the actuator 75 may include upper and lower panels 73, an air bag 74, an actuator 75, an air inlet 76a, and an air outlet 76b.

The upper and lower panels 73 may respectively be disposed at upper and lower portions of the backing layer adjusting unit 71a to be connected to the air bag 74. The upper and lower panels 73 may be connected to the air bag 74 such that air inside the backing layer adjusting unit 71a does not leak to the outside.

In addition, the upper and lower panels 73 may be formed of a rigid material such that the backing layer adjusting unit 71a expands in volume only in the horizontal direction, not in the vertical direction. For example, a material used to form the backing layer adjusting unit 71a may include metal or carbon allotrope such as carbon nanotube (CNT), graphite, and graphene. In addition, the upper and lower panels 73 may be formed of various materials suitable for volumetric expansion of the backing layer adjusting unit 71a only in the horizontal direction and preventing leakage of air to the outside.

The air bag 74 may be connected to the upper and lower panels 73 and air may be introduced into and discharged out of the air bag 74 by the actuator 75. In addition, the inside of the air bag 74 may be shielded from the outside such that air flows into and out of the air bag 74 through only the actuator 75. In addition, the air bag 74 may have elasticity suitable for volumetric change in accordance with air introduced and discharged by the actuator 75.

For example, the air bag 74 may be formed of a plastic or rubber. Various other materials that may shield internal air from the outside and have elasticity suitable for volumetric expansion may also be used to form the air bag 74.

The actuator 75 may expand the volume of the air bag 74 by introducing external air into the air bag 74 by increasing a hydraulic pressure according to a control signal and may contract the volume of the air bag 74 by discharging internal air out of the air bag 74 by decreasing the hydraulic pressure, thereby providing power to control a curvature of the first backing layer. However, the actuator 75 is exemplarily described, and various other devices capable of introducing external air into the air bag 74 and discharging internal air out of the air bag 74 may also be used.

The air inlet 76a is disposed inside the air bag 74 and is connected to the actuator 75 so as to transfer external air provided by the actuator 75 into the air bag 74 or transfer internal air of the air bag 74 to the actuator 75 such that the actuator 75 discharges the internal air of the air bag 74 to the outside, in accordance with the change in the hydraulic pressure.

In addition, the air inlet 76a may have various other shapes suitable for allowing the actuator 75 to introduce external air into the air bag 74 or to discharge internal air out of the air bag 74. For example, the air inlet 76a may be formed of a metal or plastic.

The air outlet 76b is disposed outside the upper and lower panels 73 and the air bag 74 and is connected to the actuator 75 so as to transfer external air to the actuator 75 or discharge internal air of the air bag 74 provided by the actuator 75, in accordance with the change in the hydraulic pressure.

In addition, the air outlet 76b may have various other shapes suitable for allowing the actuator 75 to introduce external air into the air bag 74 or to discharge internal air out of the air bag 74. In addition, a material used to form the air outlet 76b may be the same as or different form that used to form the air inlet 76a.

As illustrated in FIG. 13A, when a controller receives an input signal to diagnose a region to be diagnosed in a long focal length, the controller transmits a control signal to the actuator 75. Then, an inner hydraulic pressure of the actuator 75 is reduced, and the actuator 75 draws internal air of the air bag 74. Then, the internal air of the air bag 74 may be transferred to the actuator 75 through the air inlet 76a, and the actuator 75 may discharge the air to the outside through the air outlet 76b. Then, as the air bag 74 contracts in volume only in the horizontal direction, the interval between the barrier walls decreases, thereby decreasing the curvature of the first backing layer. Accordingly, the curvature of the piezoelectric layer 30 disposed on the top surface of the first backing layer and having flexibility and the curvature of the matching layer 20 disposed on the top surface of the piezoelectric layer 30 and having flexibility decrease in accordance with the decreased curvature of the first backing layer. As a result, the focal length of the ultrasonic probe increases.

On the contrary, as illustrated in FIG. 13B, when the controller receives an input signal to diagnose a region to be diagnosed in a short focal length, the controller transmits a control signal to the actuator 75. Then, an inner hydraulic pressure of the actuator 75 is increased, and the actuator 75 draws external air of the air bag 74. Then, external air transferred by the actuator 75 via the air inlet 76a is introduced into the air bag 74, and an internal pressure of the air bag 74 increases. Accordingly, the volume of the air bag 74 may increase corresponding to an external pressure. Then, as the air bag 74 expands in volume only in the horizontal direction, the interval between the barrier walls increases, thereby increasing the curvature of the first backing layer. Accordingly, the curvature of the piezoelectric layer 30 disposed on the top surface of the first backing layer and having flexibility and the curvature of the matching layer 20 disposed on the top surface of the piezoelectric layer 30 and having flexibility increase in accordance with the increased curvature of the first backing layer. As a result, the focal length of the ultrasonic probe decreases.

Figure 14A:
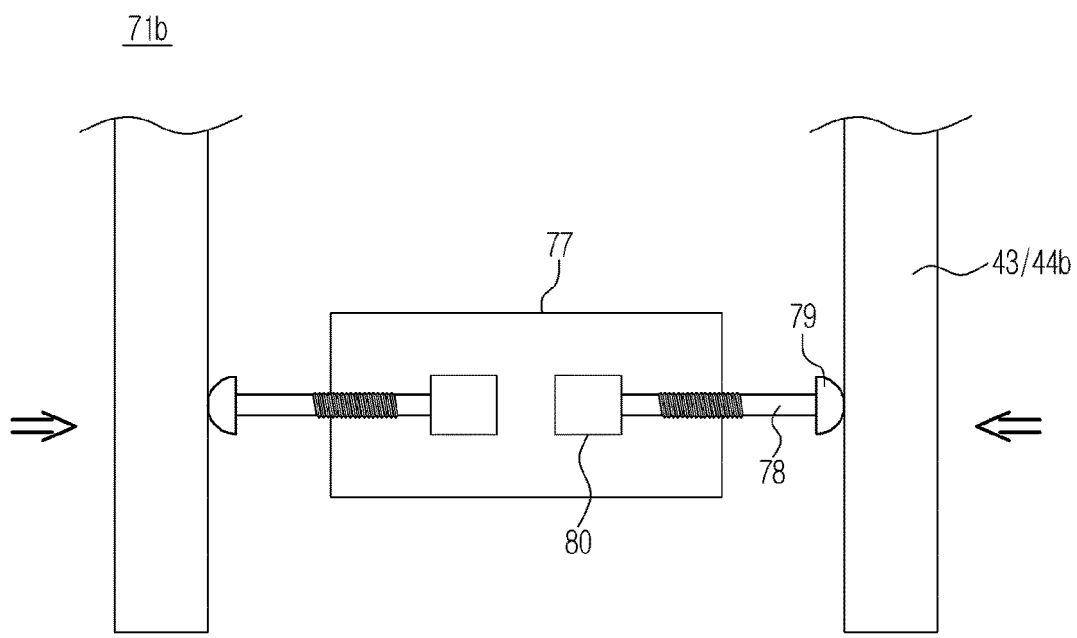
FIG. 14A is a conceptual diagram illustrating a method of decreasing a curvature of a backing layer without vertical movement of a backing layer adjusting unit including a motor and a lead screw according to an embodiment of the present invention.
Figure 14B:
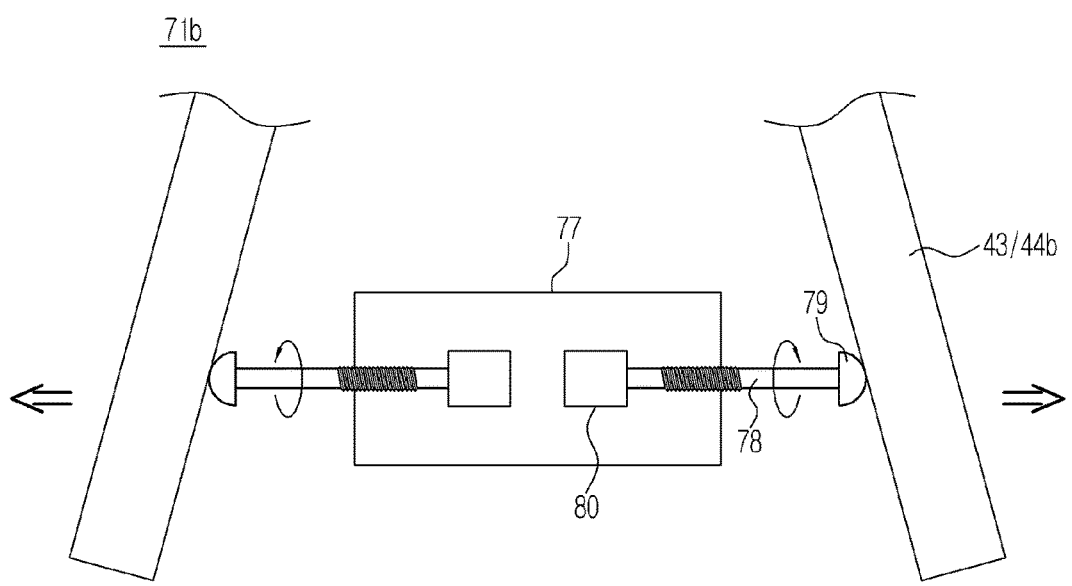
FIG. 14B is a conceptual diagram illustrating a method of increasing a curvature of a backing layer without vertical movement of a backing layer adjusting unit including a motor and a lead screw according to an embodiment of the present invention.

FIG. 14A is a conceptual diagram illustrating a method of decreasing a curvature of a backing layer without vertical movement of a backing layer adjusting unit 71b including a motor 80 and a lead screw 78 according to an embodiment of the present invention. FIG. 14B is a conceptual diagram illustrating a method of increasing the curvature of the backing layer without vertical movement of the backing layer adjusting unit 71b including the motor 80 and the lead screw 78.

The backing layer adjusting unit 71b including the motor and the lead screw 78 may include a housing 77, a motor 80, a screw 78, and a packing 79.

The housing 77 may include various parts required for driving of the backing layer adjusting unit 71b. Particularly, the housing 77 may include a motor 80 or may have a spiral surface corresponding to a metal wing of the screw 78.

In a state of being connected to the screw 78, the motor 80 may perform a fastening operation in accordance with a control signal from the controller to move the screw 78 toward both sides of the backing layer adjusting unit 71b, thereby increasing the curvature of the first backing layer. On the contrary, the motor 80 may perform a loosening operation to move the screw 78 toward the backing layer adjusting unit 71b, thereby decreasing the curvature of the first backing layer. The motor 80 may be a permanent magnet, a servo motor, a brushless (BL) motor, a DC motor, or an AC motor. In addition, the motor 80 may also have various other shapes suitable for changing the curvature of the first backing layer by providing power to the backing layer using the screw 78.

The screw 78 is a power conversion element that includes a metal wing having a spiral surface at an end of a rotation shaft and converts rotational force into linear force while rotating, thereby moving in the axial direction. The screw 78 receives power from the motor 80 and rotates along the spiral surface formed in the housing 77 to move toward both sides of the backing layer adjusting unit 71b or toward the center of the backing layer adjusting unit 71b.

For example, the screw 78 may be a lead screw 78. In addition, the screw 78 may also have various other shapes suitable for adjusting the curvature of the first backing layer by receiving power from the motor 80.

In addition, the screw 78 may be formed of a metal or plastic. In addition, various other rigid materials may also be used to form the screw 78 as long as the screw 78 may move along the spiral surface of the housing 77 by using power received from the motor 80.

The packing 79 may be a power conversion element provided at an end of the screw 78 and transferring linear force of the screw 78, which moves by converting the rotational force received from the motor 80 into the linear force, to the backing layer. The packing 79 may be formed of rubber having elasticity to relieve impact applied to the backing layer. In addition, the packing 79 may be formed of various other materials and may have various shapes suitable for transferring the linear force to the backing layer while relieving impact.

As illustrated in FIG. 14A, when the controller receives an input signal to diagnose a region to be diagnosed in a long focal length, the controller transmits a control signal to the motor 80. Then, the motor 80 may perform a loosening operation and transfer rotational force to the screw 78. The screw 78 converts the rotational force received from the motor 80 into linear force using a rotating wing of the screw 78 and the spiral surface of the housing 77 corresponding to the rotating wing of the screw 78. The screw 78 may move toward the center of the backing layer adjusting unit 71b by using the linear force. In addition, as screw 78 moves toward the backing layer adjusting unit 71b, the interval between the barrier walls decreases, thereby decreasing the curvature of the first backing layer. In addition, the curvature of the piezoelectric layer 30 disposed on the top surface of the first backing layer and having flexibility and the curvature of the matching layer 20 disposed on the top surface of the piezoelectric layer 30 and having flexibility decrease in accordance with the decreased curvature of the first backing layer. As a result, the focal length of the ultrasonic probe increases.

On the contrary, as illustrated in FIG. 14B, when the controller receives an input signal to diagnose a region to be diagnosed in a short focal length, the controller transmits a control signal to the motor 80. Then, the motor 80 may perform a fastening operation and transfer rotational force thereof to the screw 78. The screw 78 converts the rotational force received from the motor 80 into linear force using the rotating wing of the screw 78 and the spiral surface of the housing 77 corresponding to the rotating wing of the screw 78. The screw 78 may move toward both sides of the backing layer adjusting unit 71b by using the linear force. In addition, as the packing 79 transfers the linear force of the screw 78, which moves to the both sides of the backing layer adjusting unit 71b, the interval between the barrier walls increases, thereby increasing the curvature of the first backing layer. In addition, the curvature of the piezoelectric layer 30 disposed on the top surface of the first backing layer and having flexibility and the curvature of the matching layer 20 disposed on the top surface of the piezoelectric layer 30 and having flexibility increase in accordance with the increased curvature of the first backing layer. As a result, the focal length of the ultrasonic probe decreases.

Figure 15A:
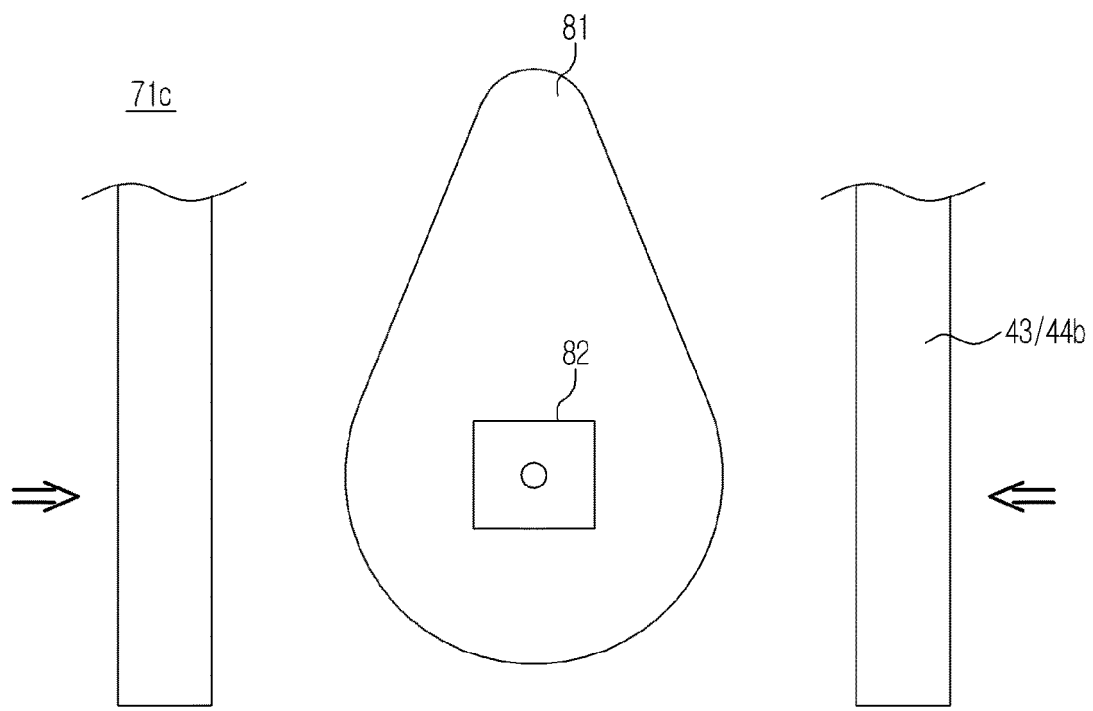
FIG. 15A is a conceptual diagram illustrating a method of decreasing a curvature of a backing layer without vertical movement of a backing layer adjusting unit including a motor and a cam according to an embodiment of the present invention.
Figure 15B:
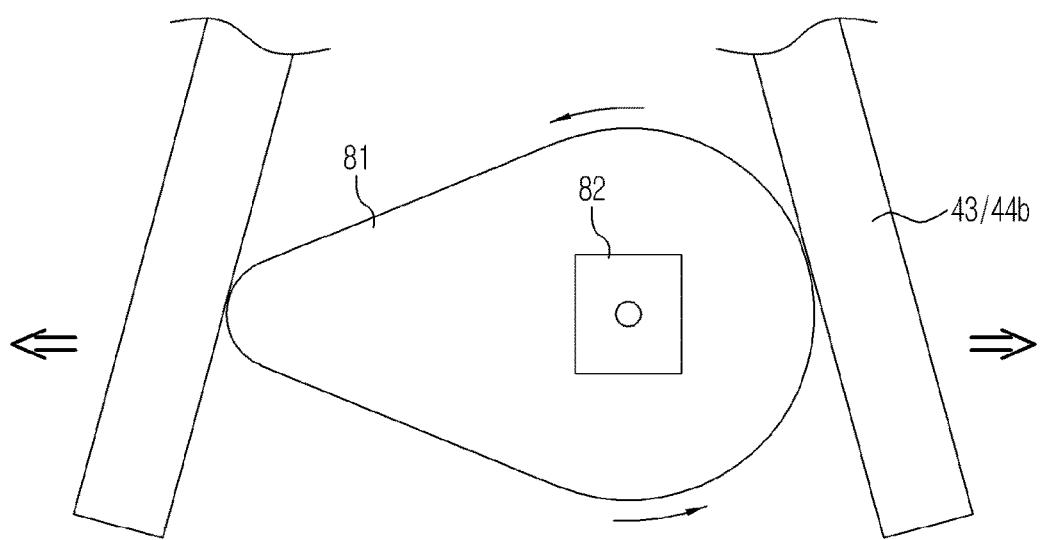
FIG. 15B is a conceptual diagram illustrating a method of increasing a curvature of a backing layer without vertical movement of a backing layer adjusting unit including a motor and a cam according to an embodiment of the present invention.

FIG. 15A is a conceptual diagram illustrating a method of decreasing a curvature of a backing layer without vertical movement of a backing layer adjusting unit 71c including a motor 82 and a cam 81 according to an embodiment of the present invention. FIG. 15B is a conceptual diagram illustrating a method of increasing the curvature of the backing layer without vertical movement of the backing layer adjusting unit 71c including the motor 82 and the cam 81.

The backing layer adjusting unit 71c may include a cam 81 and a motor 82.

The cam 81, which is a plate-shaped device having a particular shape or groove and performing rotational motion or reciprocating motion, may be a power conversion element for transforming a rotational motion or a reciprocating motion into another reciprocating motion or a rocking motion.

Particularly, as illustrated in FIG. 15A, a horizontal axial length of the cam 81 may be different from a vertical axial length thereof, and the cam 81 may have a gently curved external surface and contact the backing layer. Since the horizontal axial length of the cam 81 is different from the vertical axial length thereof, and the external surface of the cam 81 contacts the backing layer, the interval between the barrier walls 44b may increase and decrease while the motor 82 rotates.

The motor 82 performs a rotational motion in accordance with a control signal from the controller, in a state of being connected to the cam 81 and transfers a rotational force to the cam 81 to increase or decrease the curvature of the first backing layer. The motor 82 may be a permanent magnet, a servo motor, a brushless (BL) motor, a DC motor, or an AC motor. In addition, the motor 82 may also have various other shapes suitable for changing the curvature of the first backing layer by providing the rotational force to the cam 81.

As illustrated in FIG. 15A, when the controller receives an input signal to diagnose a region to be diagnosed in a long focal length, the controller transmits a control signal to the motor 82. Then, the motor 82 may perform a rotational motion and transfer rotational force to the cam 81. When a shorter portion of the cam 81 contacts the backing layer, the curvature of the first backing layer decreases. In addition, the curvature of the piezoelectric layer 30 disposed on the top surface of the first backing layer and having flexibility and the curvature of the matching layer 20 disposed on the top surface of the piezoelectric layer 30 and having flexibility decrease in accordance with the decreased curvature of the first backing layer. As a result, the focal length of the ultrasonic probe increases.

On the contrary, as illustrated in FIG. 15B, when the controller receives an input signal to diagnose a region to be diagnosed in a short focal length, the controller transmits a control signal to the motor 82. Then, the motor 82 may perform a rotational motion and transfer rotational force to the cam 81. When a longer portion of the cam 81 contacts the backing layer, the curvature of the first backing layer increases. In addition, the curvature of the piezoelectric layer 30 disposed on the top surface of the first backing layer and having flexibility and the curvature of the matching layer 20 disposed on the top surface of the piezoelectric layer 30 and having flexibility increase in accordance with the increased curvature of the first backing layer. As a result, the focal length of the ultrasonic probe decreases.

Hereinafter, a method of focusing of an ultrasonic probe having different focal zones according to an embodiment of the present invention will be described.

Figure 16:
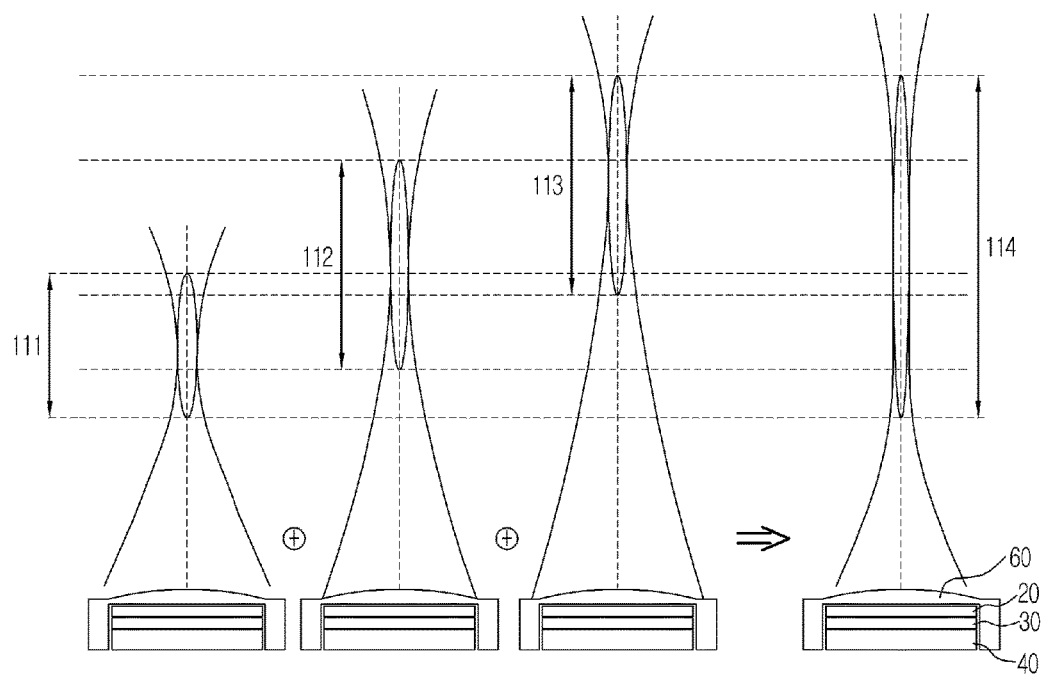
FIG. 16 is a conceptual diagram illustrating a method of merging three ultrasonic images acquired using different focal zones adjusted by changing a curvature of a backing layer corresponding to three segmented regions according to an embodiment of the present invention.
Figure 17:
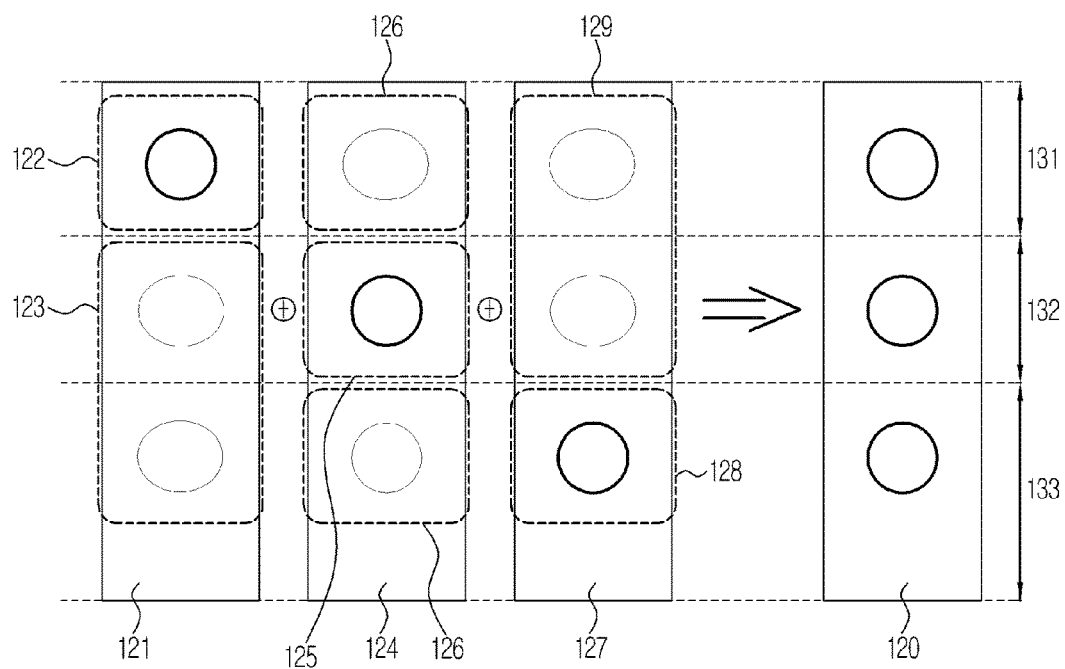
FIG. 17 is a conceptual diagram illustrating a method of merging three ultrasonic images in which ultrasonic waves are respectively focused on different regions according to an embodiment of the present invention.

FIG. 16 is a conceptual diagram illustrating a method of merging three ultrasonic images acquired using different focal zones adjusted by changing a curvature of a backing layer corresponding to three segmented regions according to an embodiment of the present invention. FIG. 17 is a conceptual diagram illustrating a method of merging three ultrasonic images in which ultrasonic waves are respectively focused on different regions according to an embodiment of the present invention.

As illustrated in FIG. 16, as a curvature of an acoustic module increases, a focal distance of the acoustic module may decrease (111). As the curvature of the acoustic module decreases, the focal distance of the acoustic module may increase (112). In addition, the acoustic module may have a maximum focal distance at a minimum curvature (113).

Ultrasonic images acquired using ultrasonic signals received from three segmented regions may be merged into a single image by an image processor (114). The merged image may have an increased focal distance (114).

Particularly, as illustrated in FIG. 17, when the acoustic module has a first curvature that is a higher curvature (121), ultrasonic signals are focused on one region 122 closer to the acoustic module (131), and the other region 123 is out of focus. In addition, when the acoustic module has a second curvature that is a middle curvature (124), ultrasonic signals are focused on one region 125 at a mid-point (132) between the acoustic module and a target, and the other region 126 is out of focus. In addition, when the acoustic module has a third curvature that is a lower curvature (127), ultrasonic signals are focused on one region 128 farther from the acoustic module (133), and the other region 129 is out of focus.

Then, only the focused regions are respectively extracted from the three ultrasonic images and merged to acquire an ultrasonic image 120 in which the closer region 131, the mid region 132, and the farther region 133 are focused.

Hereinafter, a method of acquiring an ultrasonic image having a wide focal zone by changing a focal zone of an ultrasonic probe according to an embodiment of the present invention will be described with reference to FIG. 18

Figure 18:
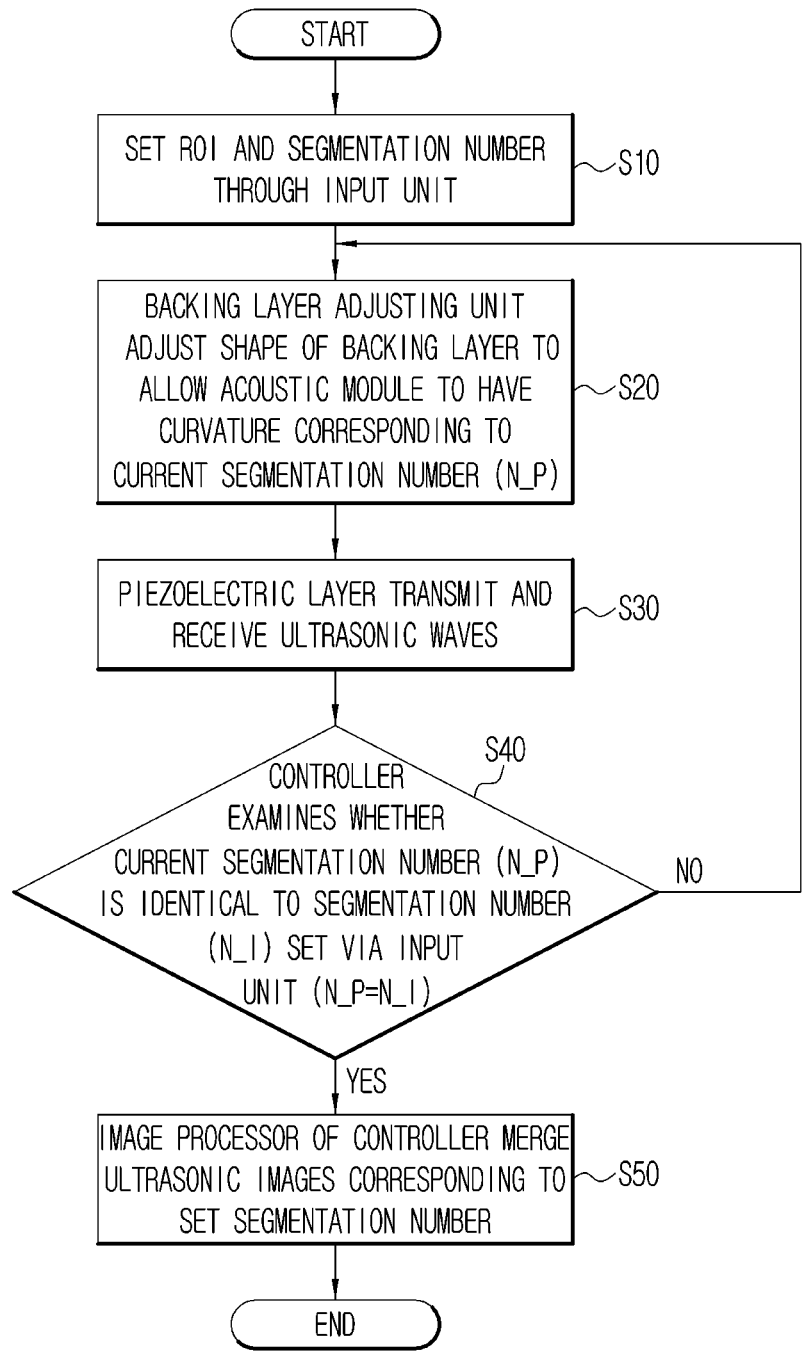
FIG. 18 is a flowchart illustrating a method of merging ultrasonic images by setting a region of interest (ROI) and a segmentation number (n_i) according to an embodiment of the present invention.

FIG. 18 is a flowchart illustrating a method of merging ultrasonic images by setting a region of interest (ROI) and a segmentation number (n_i).

When a region of interest (ROI) of an object and a segmentation number (n_i) are set through an input unit (S10), a backing layer adjusting unit may adjust the shape of a backing layer such that an acoustic module has a curvature corresponding to a first segmentation number (S20). Then, a piezoelectric layer may emit ultrasonic waves to a region to be diagnosed and receive echo signals reflected by the region (S30). Then, the controller may examine whether a current segmentation number (n_p) is identical to the segmentation number (n_i) set through the input unit, i.e., whether n_p=n_i (S 40).

If the current segmentation number (n_p) is less than the segmentation number (n_i) set through the input unit, operations S20 and S30 may be performed. However, if the current segmentation number (n_p) is identical to the segmentation number (n_i) set through the input unit, an image processor of the controller may merge ultrasonic images corresponding to the set segmentation number (n_i).

As is apparent from the above description, the ultrasonic probe may provide efficient focusing by adjusting the focal zone by changing curvatures of the matching layer and the piezoelectric layer in accordance with a changed curvature of the backing layer.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ultrasonic probe comprising:
   a matching layer that is flexible;
   a piezoelectric layer that is flexible and disposed adjacent to the matching layer;
   a first backing layer that is flexible and disposed adjacent to the piezoelectric layer;
   a second backing layer disposed adjacent to the first backing layer and comprising a plurality of backing material layers; and
   second backing layer adjusting units respectively disposed between every two of the plurality of the stacked backing material layers of the second backing layer and configured to adjust an interval distance between the every two of the plurality of backing material layers,
   wherein the matching layer, the piezoelectric layer, and the first backing layer are stacked in a first direction, and the plurality of backing material layers of the second backing layer are stacked in a second direction perpendicular to the first direction.

2. The ultrasonic probe according to claim 1, further comprising fixing units disposed at both sides of the plurality of backing material layers of the second backing layer and fixing the plurality of backing material layers.

3. The ultrasonic probe according to claim 1, wherein a central backing material layer among the plurality of backing material layers of the second backing layer is fixed to the first backing layer not to move horizontally.

4. The ultrasonic probe according to claim 1, wherein the second backing layer adjusting units respectively adjust the interval distance between the every two of the plurality of backing material layers without moving vertically.

5. The ultrasonic probe according to claim 1, wherein the second backing layer adjusting units respectively adjust the interval distance between the every two of the plurality of backing material layers by moving vertically.

6. The ultrasonic probe according to claim 1, wherein the piezoelectric layer is formed of a ceramic complex.

7. The ultrasonic probe according to claim 1, wherein the piezoelectric layer comprises a plurality of piezoelectric layers arranged in a matrix array, a linear array, a convex array, a phased array, or a concave array.

8. The ultrasonic probe according to claim 1, further comprising a controller to control operations of the second backing layer adjusting units and the piezoelectric layer.

9. The ultrasonic probe according to claim 8, wherein the controller controls a focal zone of ultrasonic waves by adjusting the second backing layer adjusting units.

10. An ultrasonic probe comprising:
    a matching layer that is flexible;
    a piezoelectric layer that is flexible and disposed adjacent to the matching layer;
    a first backing layer that is flexible and disposed adjacent to the piezoelectric layer, comprising a ceiling disposed parallel to the piezoelectric layer and barrier walls disposed perpendicularly to the piezoelectric layer;

a second backing layer disposed adjacent to the first backing layer and comprising a plurality of backing material layers; and a first backing layer adjusting unit disposed adjacent to the second backing layer between the barrier walls of the first backing layer, and configured to adjust an interval distance between the barrier walls of the first backing layer, wherein the matching layer, the piezoelectric layer, and the ceiling of the first backing layer are stacked in a first direction, and the plurality of backing material layers of the second backing layer are stacked in a second direction perpendicular to the first direction.

11. The ultrasonic probe according to claim 10, wherein the first backing layer adjusting unit adjusts the interval distance between the barrier walls of the first backing layer without moving vertically.

12. The ultrasonic probe according to claim 10, wherein the piezoelectric layer is formed of a ceramic complex.

13. The ultrasonic probe according to claim 10, wherein the piezoelectric layer comprises a plurality of piezoelectric layers arranged in a matrix array, a linear array, a convex array, a phased array, or a concave array.

14. The ultrasonic probe according to claim 10, further comprising a controller to control operations of the first backing layer adjusting unit and the piezoelectric layer.

15. The ultrasonic probe according to claim 14, wherein the controller controls a focal zone of ultrasonic waves by adjusting the first backing layer adjusting unit.

* * * * *